US011001581B2

(12) United States Patent
Laiho et al.

(10) Patent No.: US 11,001,581 B2
(45) Date of Patent: May 11, 2021

(54) COMPOUNDS WHICH INHIBIT RNA POLYMERASE, COMPOSITIONS INCLUDING SUCH COMPOUNDS, AND THEIR USE

(71) Applicants: THE JOHNS HOPKINS UNIVERSITY, Baltimore, MD (US); LIEBER INSTITUTE, INC., Baltimore, MD (US)

(72) Inventors: Marikki Laiho, Baltimore, MD (US); Laureen Colis, Hamden, CT (US); James C. Barrow, Arnold, MD (US); Glen Ernst, Bear, DE (US); Sara Sanders, St. Louis, MO (US)

(73) Assignee: The Johns Hopkins University and Lieber Institute, Inc., Baltimore, MD (US)

( * ) Notice: Subject to any disclaimer, the term of this patent is extended or adjusted under 35 U.S.C. 154(b) by 0 days.

(21) Appl. No.: 15/126,588

(22) PCT Filed: Mar. 20, 2015

(86) PCT No.: PCT/US2015/021699
§ 371 (c)(1),
(2) Date: Sep. 16, 2016

(87) PCT Pub. No.: WO2015/143293
PCT Pub. Date: Sep. 24, 2015

(65) Prior Publication Data
US 2017/0081322 A1 Mar. 23, 2017

Related U.S. Application Data

(60) Provisional application No. 61/968,079, filed on Mar. 20, 2014, provisional application No. 62/062,197, filed on Oct. 10, 2014.

(51) Int. Cl.
| | | |
|---|---|---|
| C07D 471/04 | (2006.01) | |
| A61P 35/00 | (2006.01) | |
| A61K 31/519 | (2006.01) | |
| A61K 31/5377 | (2006.01) | |
| A61K 45/06 | (2006.01) | |

(52) U.S. Cl.
CPC .......... *C07D 471/04* (2013.01); *A61K 31/519* (2013.01); *A61K 31/5377* (2013.01); *A61K 45/06* (2013.01)

(58) Field of Classification Search
None
See application file for complete search history.

(56) References Cited

U.S. PATENT DOCUMENTS

| 4,450,150 A | 5/1984 | Sidman |
| 5,908,840 A | 6/1999 | Trova |
| 8,680,107 B2 | 3/2014 | Laiho et al. |
| 2009/0163545 A1 | 6/2009 | Goldfarb |
| 2010/0179155 A1 | 7/2010 | Laiho |

FOREIGN PATENT DOCUMENTS

| WO | 2008/155441 A1 | 12/2008 |
| WO | 2008/155468 A1 | 12/2008 |

OTHER PUBLICATIONS

Banker, Gilbert. Modern Pharmaceutics 3rd ed. Marcel Dekker, Inc. New York, 1996.*
STN Registry File. Registry Nos. 896688-29-2 and 896705-25-2 entered Jul. 28, 2006.*
Compendium of Chemical Terminology, 2nd ed. (the "Gold Book"). Compiled by A. D. McNaught and A. Wilkinson. Blackwell Scientific Publications, Oxford (1997) Web<https://doi.org/10.1351/goldbook>.*
Peltonen, K., et al., "A targeting modality for destruction of RNA polymerase I that possesses anticancer activity" Cancer Cell, Jan. 13, 2014, vol. 25, pp. 77-90.
EP Search Report and Written Opinion in EP Appln. No. 15765295. 9, dated Jul. 14, 2017, 6 pages.
International Search Report and Written Opinion in PCT Appln. No. PCT/US2015/021699, dated Jun. 29, 2015, 8 pages.
Boulon, et al., The nucleolus under stress. Mol Cell. Oct. 22, 2010;40(2):216-27.
Bywater, et al., Dysregulation of the basal RNA polymerase transcription apparatus in cancer. Nat Rev Cancer. May 2013;13(5)299-314.
Comai, et al., Mechanism of RNA polymerase I transcription. Adv Protein Chem. 2004; 67: 123-155.
Drygin, et al., Targeting RNA polymerase I with an oral small molecule CX-5461 inhibits ribosomal RNA synthesis and solid tumor growth. Cancer Res. Feb. 15, 2011;71(4):1418-30.
Grummt, et al., Wisely chosen paths-regulation of rRNA synthesis. FEBS J. Nov. 2010;277(22):4626-39.
Haag, et al., RNA polymerase I: a multifunctional molecular machine. Cell. Dec. 2007; 131(7): 1224-1225.
Haddach, et al., Discovery of CX-5461, the first direct and selective inhibitor of RNA polymerase I, for cancer therapeutics. ACS Med Chem Lett. Jul. 12, 2012; 3(7): 602-606.

(Continued)

*Primary Examiner* — Emily A Bernhardt
*Assistant Examiner* — Laura M Daniel
(74) *Attorney, Agent, or Firm* — Fish & Richardson P.C.

(57) ABSTRACT

RNA polymerase I (Pol I) is a dedicated polymerase for the transcription of the 47S ribosomal RNA precursor subsequently processed into the mature 5.8S, 18S and 28S ribosomal RNAs and assembled into ribosomes in the nucleolus. Pol I activity is commonly deregulated in human cancers. Based on the discovery of lead molecule BMH-21, a series of pyridoquinazolinecarboxamides were synthesized as inhibitors of Pol I and activators of the destruction of RPA194, the Pol I large catalytic subunit protein. The present invention identifies a set of bioactive compounds, including purified stereoisomers, that potently cause RPA194 degradation that function in a tightly constrained chemical space. Pharmaceutical compositions comprising these compounds and their uses in cancer and other Pol I related diseases is also provided.

11 Claims, 6 Drawing Sheets

(56) References Cited

OTHER PUBLICATIONS

Hernandez-Verdun, et al., Nucleolus: from structure to dynamics. Histochem Cell Biol. Jan. 2006;125(1-2):127-37.

Montanaro, et al., Nucleolus, ribosomes, and cancer. Am J Pathol. Aug. 2008;173(2):301-10.

Mukherjee, et al., Drug-DNA Intercalation: From Discovery to the Molecular Mechanism. Adv Protein Chem Struct Biol. 2013;92:1-62.

Peltonen, et al., Identification of novel p53 pathway activating small-molecule compounds reveals unexpected similarities with known therapeutic agents. PLoS One. Sep. 27, 2010;5(9):e12996.

Bywater, et al., Inhibition of RNA polymerase I as a therapeutic strategy to promote cancer-specific activation of p53. Cancer Cell. Jul. 10, 2012;22(1):51-65.

Russell, et al., The RNA polymerase I transcription machinery. Biochem Soc Symp. 2006;(73):203-16.

Trott, et al., AutoDock Vina: improving the speed and accuracy of docking with a new scoring function, efficient optimization, and multithreading. J Comput Chem. Jan. 30, 2010; 31(2): 455-461.

Colis, et al., Design, Synthesis and Structure-Activity Relationships of Pyridoquinazolinecarboxamides as RNA Polymerase I Inhibitors. J Med Chem. Jun. 12, 2014;57(11):4950-61.

Drygin, et al., The RNA polymerase I transcription machinery: an emerging target for the treatment of cancer. Annu Rev Pharmacol Toxicol. 2010;50:131-56.

\* cited by examiner

COMPOUNDS WHICH INHIBIT RNA POLYMERASE, COMPOSITIONS INCLUDING SUCH COMPOUNDS, AND THEIR USE

CROSS-REFERENCE TO RELATED APPLICATIONS

This application is a 35 U.S.C. § 371 U.S. national entry of International Application PCT/US2015/021699, having an international filing date of Mar. 20, 2015, which claims the benefit of U.S. Provisional Application No. 61/968,079, filed Mar. 20, 2014, and U.S. Provisional Application No. 62/062,197, filed Oct. 10, 2014, the content of each of the aforementioned applications is herein incorporated by reference in their entirety.

BACKGROUND OF THE INVENTION

Ribosomal (r) DNA is the most highly transcribed genomic region of the human genome and occurs in a dedicated subcellular compartment, the nucleolus. Transcription of rRNA is mediated by RNA polymerase I (Pol I) that transcribes the multicopy rDNA gene to a long 47S rRNA precursor. The 47S rRNA precursor is processed through multiple steps to the 18S, 5.8S and 28S mature rRNAs requisite for the assembly of the ribosomes. Pol I transcription is initiated by binding of a multisubunit pre-initiation complex to rDNA promoter, which stochastically recruits the Pol I holocomplex. The Pol I holocomplex is composed of 14 subunits in eukaryotes, of which the subunits RPA194, RPA135 and RPA12 form the catalytically active site. Destabilization of the rDNA helix, or loss of the protein framework, will effectively stall transcription. The rate of rRNA transcription is tightly controlled by external signaling pathways that cause the assembly and binding of the preinitiation complex. Deregulation of rRNA synthesis is highly frequent in human cancers. This is due to activation of extracellular and intracellular signaling pathways and oncogenes such as Myc. Conversely, loss-of-function of tumor suppressors p53, pRB, ARF and PTEN lead to activation of Pol I transcription. Therefore, inhibitors of Pol I transcription may provide novel approaches toward cancer therapies.

Despite the key impact of Pol I contributing to cancer cell characteristics, its therapeutic exploitation has been minimal. The present inventors have recently presented the discovery of an anticancer small molecule, 12H-Benzo[g] pyrido[2,1-b]quinazoline-4-carboxamide, N-[2(dimethyl-amino)ethyl]-12-oxo (BMH-21) with a distinct mode of inhibition of Pol I compared to CX-5461 U.S. patent application Ser. No. 12/665,473, filed Mar. 1, 2010 (FIG. 1). These studies demonstrated that BMH-21 intercalates with GC-rich rDNA, inhibits Pol I and causes proteasome-mediated degradation of RPA194. BMH-21 also showed broad and potent anticancer activity in NCI60 cancer cell lines and reduced tumor burden in mouse xenograft assays. These studies have provided proof-of-principle confirmation that Pol I targeting is a feasible approach for cancer control.

SUMMARY OF THE INVENTION

In accordance with an embodiment, the present invention provides a compound of formula I:

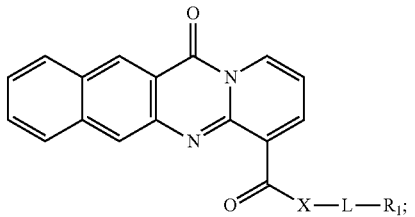

wherein X is $NR_2$;
wherein L is $R_3$ or an optionally substituted cycloamine

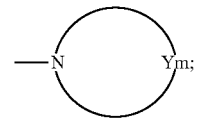

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;
when L is $R_3$, $R_3$ is a straight-chained or branched $C_2$-$C_6$ alkyl group;
when L is

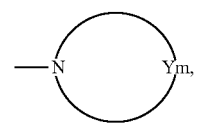

m=1-8 and each Y is independently selected from $(CH_2)_n Y^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof.

In accordance with an embodiment, the present invention provides a chirally pure stereoisomer of compound of formula I, wherein L is $R_3$ and $R_3$ is a straight-chained or branched $C_2$-$C_6$ alkyl group having at least one chiral carbon.

In accordance with another embodiment, the present invention provides compounds of formula II,

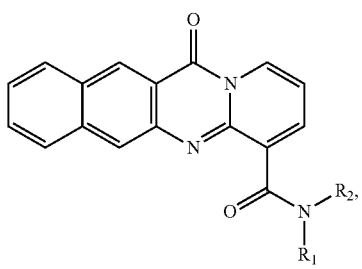

(II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group.

In accordance with another embodiment, the present invention provides a pharmaceutical composition comprising a compound of formula I and/or formula II, and a pharmaceutically acceptable carrier.

In accordance with a further embodiment, the present invention provides a method for activating upstream p53 pathways in a mammalian cell comprising contacting a cell or population of cells with a compound of formula I and/or formula II.

In accordance with still another embodiment, the present invention provides a method for modulating RNA Pol I activity in a mammalian cell comprising contacting a cell or population of cells with a compound of formula I and/or formula II.

In accordance with yet a further embodiment, the present invention provides a method for treating cancer in a subject comprising administering to the subject a pharmaceutical composition comprising a compound of formula I and/or formula II.

In accordance with an embodiment, the present invention provides a method for treating cancer in a subject comprising administering to the subject a pharmaceutical composition comprising a compound of formula I and/or formula II, and at least one other biologically active agent.

BRIEF DESCRIPTION OF THE DRAWINGS

FIG. 1 depicts the RNA Pol I inhibitor CX-5461, the BMH-21 parent molecule, and its inactive analogue BMH-21a.

DETAILED DESCRIPTION OF THE INVENTION

Figure 1:
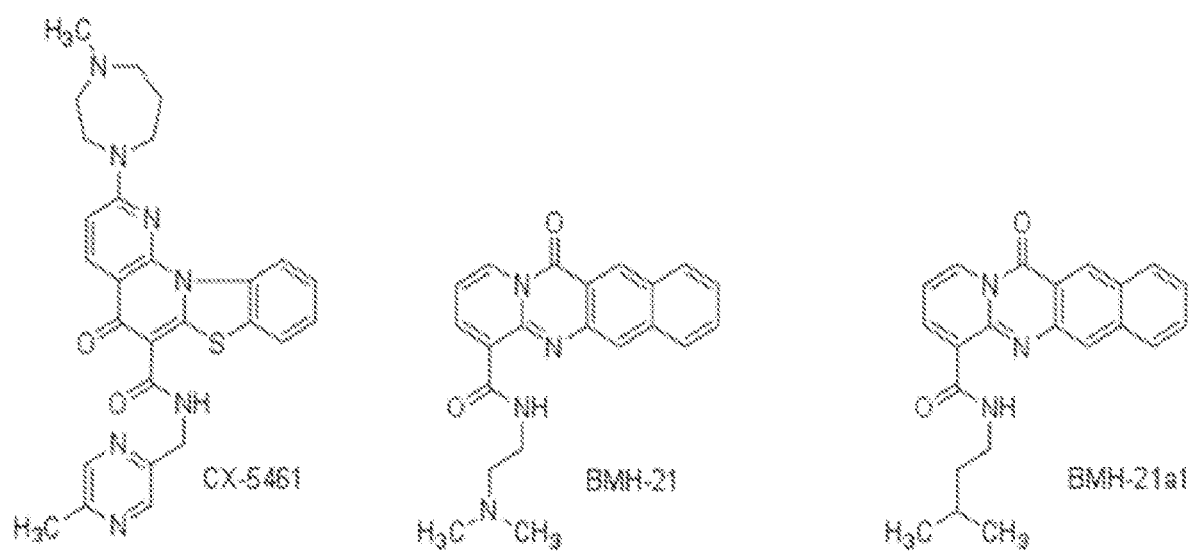
Figure 2:
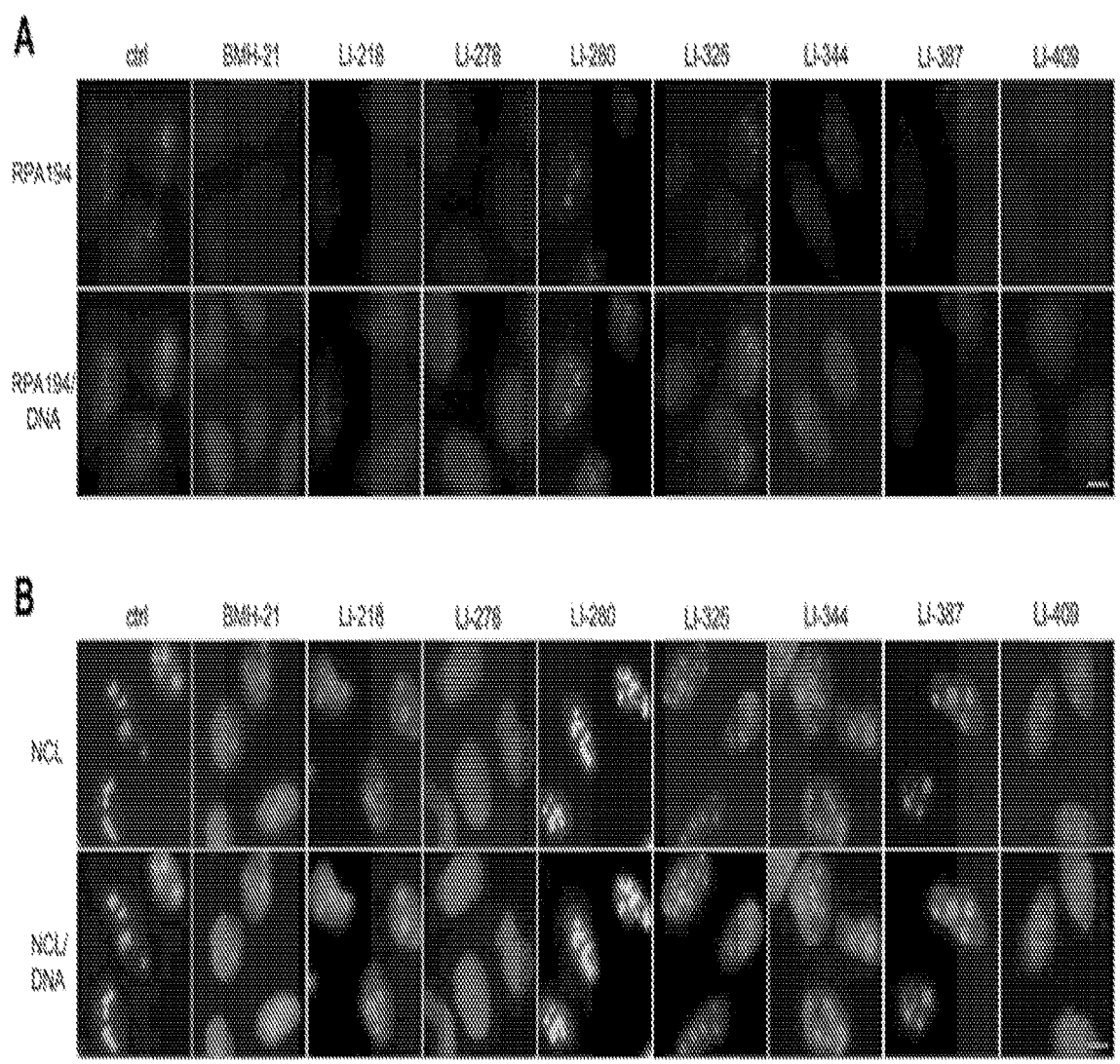
FIG. 2 shows the effect of compounds on expression and localization of RPA194 and NCL. Immunofluorescence staining of U2OS cells treated with the indicated compounds (0.5 μM) for 3 hours. Cells were stained for (A) RPA194 (red) and (B) NCL (green) and counterstained for DNA (blue). Scale bars, 10 μm.
Figure 3A:
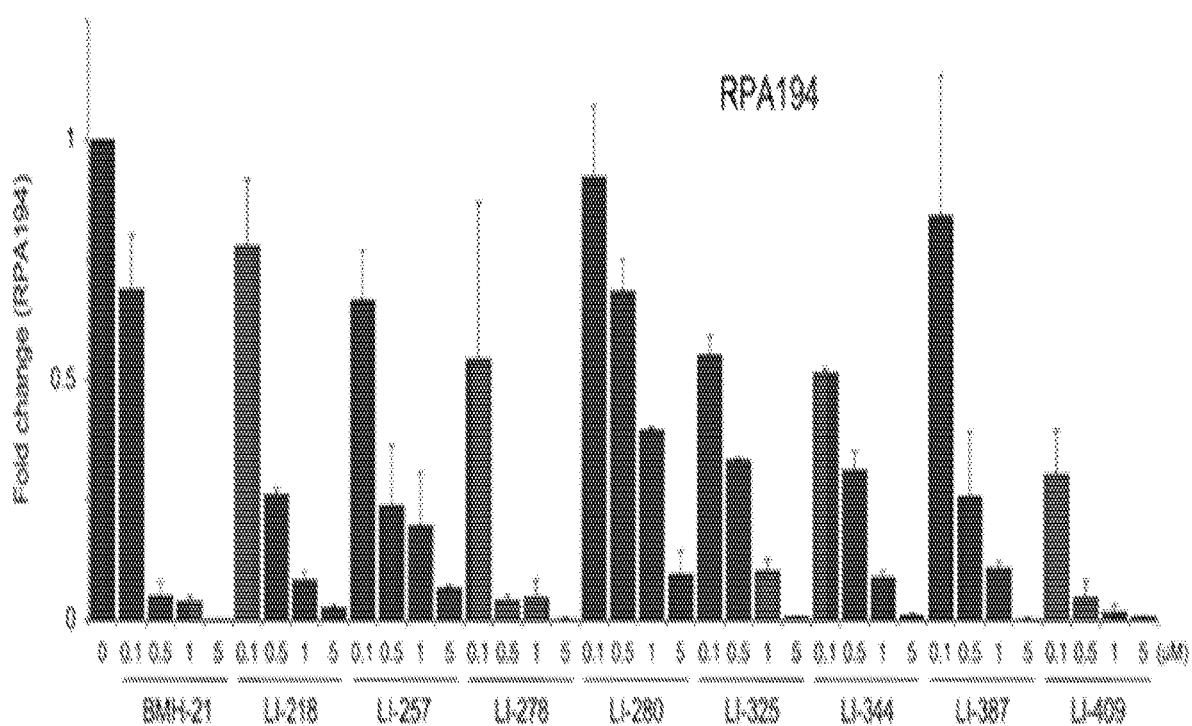
FIG. 3 depicts quantitative image analysis of expression and localization of RPA194 and NCL by derivatives. U2OS cells were treated with the compounds at 0, 0.1, 0.5, 1 and 5 μM and incubated for 3 hours. Cells were fixed and stained for (A) RPA194 and (B) NCL and counterstained for DNA and imaged using epifluorescence. Quantitative image analysis for RPA194 degradation (A) and loss of NCL nucleolar intensity was conducted based on two biological replicates and the fold change to control is shown. Error bars, s.e.m.
Figure 3B:
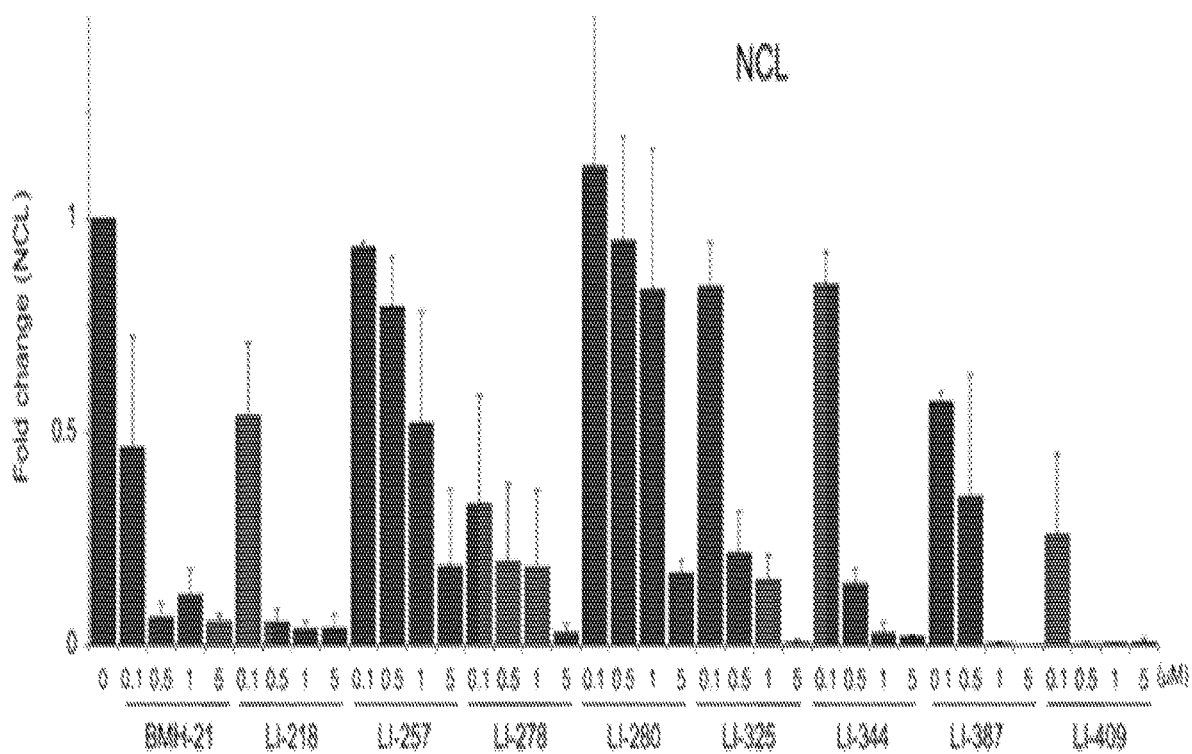
Figure 4:
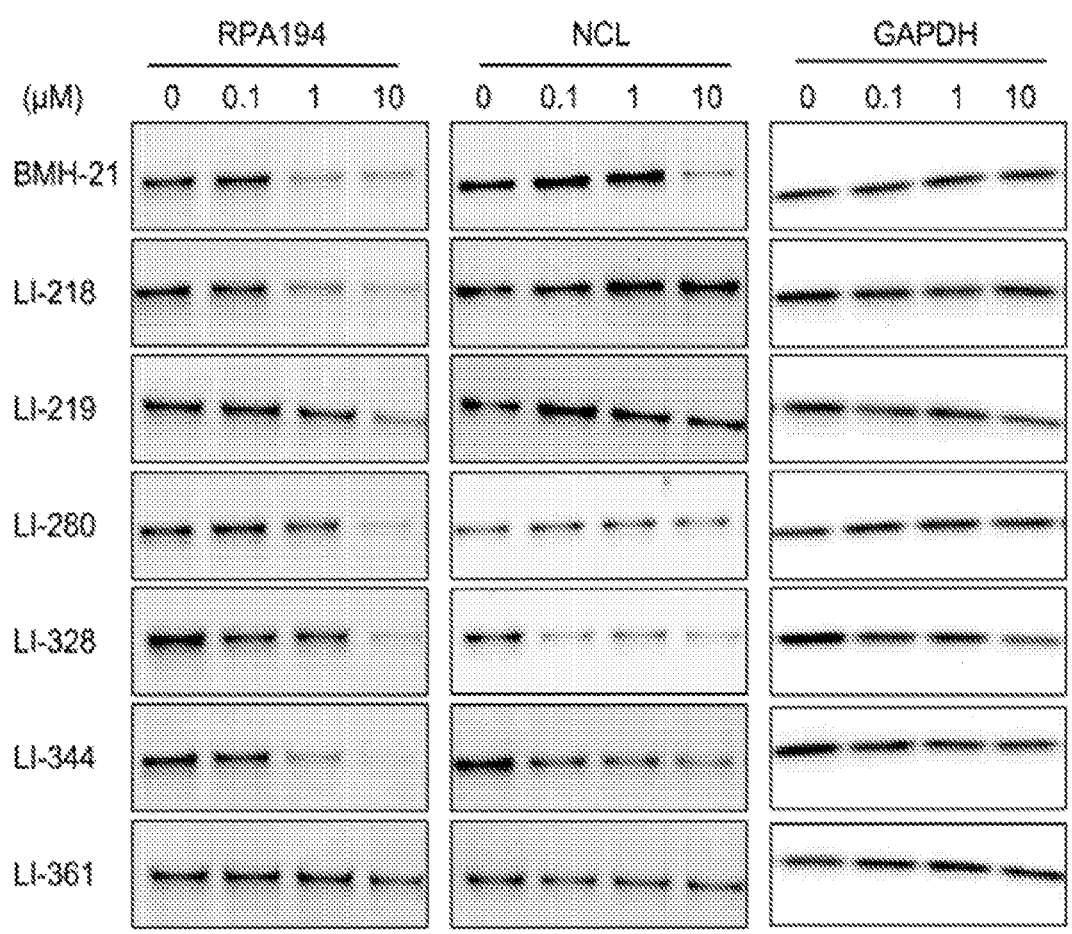
FIG. 4 shows protein expression analyses for RPA194 and NCL. U2OS cells were treated with the compounds at 0, 0.1, 1 and 10 μM and incubated for 3 h. Protein was extracted using RIPA lysis buffer and Western blotting for was conducted for RPA194, NCL and GAPDH as control.
Figure 5:
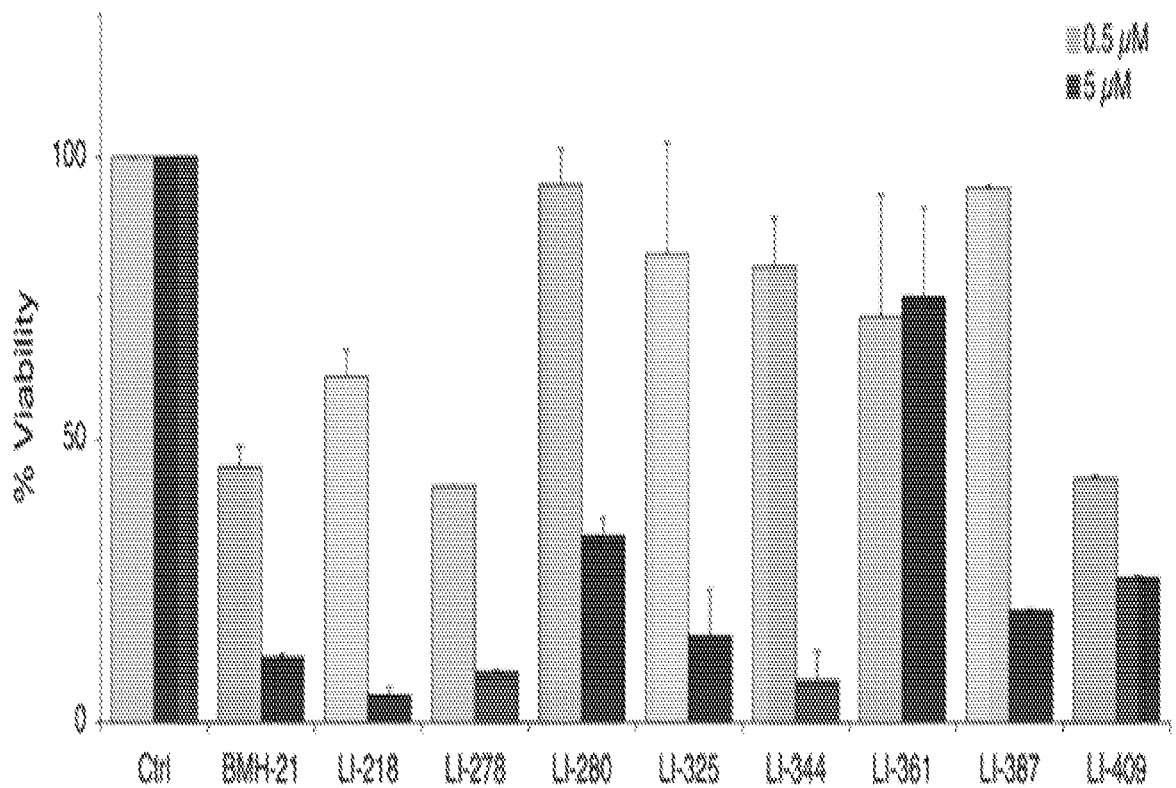
FIG. 5 depicts cell viability assays. U2OS cells were treated with the compounds at 0, 0.5, and 5 μM and incubated for 48 hours. Cell viability was determined using WST-1 assay. N=2 biological repeats, error bars s.e.m.

In accordance with one or more embodiments of the present invention, a series of BMH-21 variants were prepared and evaluated as potential novel anticancer agents that act via the repression of Pol I activity. The activity of BMH-21 is due to its ability to intercalate to GC-rich rDNA sequences, which makes it very different from other 4-ring anthracyclines, which cause DNA damage. Their intercalation modalities are also quite distinct from the anthracyclines intercalating perpendicular to the DNA helix, whereas BMH-21 intercalates in a near-parallel fashion. While previous modeling has suggested some molecular determinants for this activity, the high sensitivity to the pendant BMH-21 chain as exemplified in the compounds identified herein, suggests there may be other components to the BMH-21-DNA complex that lead to its biological activity. Notably, all near equipotent derivatives retained a predicted protonation of the terminal amine and had a basic pKa close to that of the parent at 8.6. These findings indicated that the overall charge of the inventive molecules was critical as well as maintaining the length and basic charge close to the end of the carboxamide arm. Without being limited to any particular theory or mechanism of action, these findings suggest that BMH-21 intercalates with acidic DNA through electrostatic interactions. It also raises the possibility that derivatives with more highly charged moieties may change the nature of the intercalation or that those with larger molecular sizes alter the DNA intercalation cavity. This further implies that such molecules can perturb other DNA metabolic processes.

Therefore, in accordance with an embodiment, the present invention provides a compound of formula I:

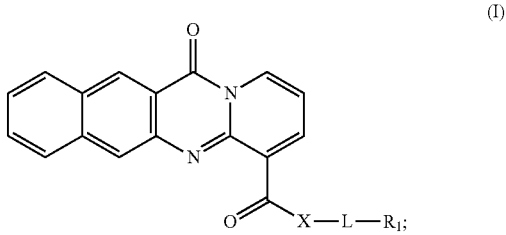

(I)

wherein X is $NR_2$;
wherein L is $R_3$ or an optionally substituted cycloamine

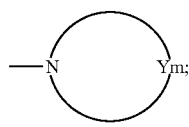

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is

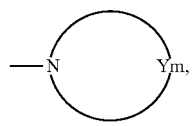

m=1-8 and each Y is independently selected from $(CH_2)_nY^1_p$ wherein n=1-8, p=0-4 and the sum of n and p is at least 2, and each $Y^1$ is independently selected from $NR_4$, O, S, or P, wherein $R_4$ is as hereinbefore defined for $R_3$, and X≠O; or a pharmaceutically acceptable salt, solvate, stereoisomer, or a prodrug thereof.

In accordance with an embodiment, the present invention provides a chirally pure stereoisomer of compound of formula I, wherein L is $R_3$ and $R_3$ is a straight-chained or branched $C_2$-$C_6$ alkyl group having at least one chiral carbon.

In accordance with another embodiment, the present invention provides compounds of formula II,

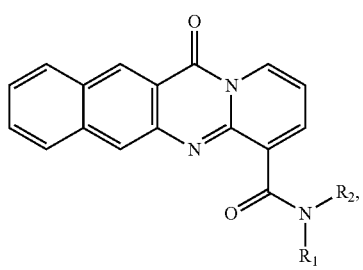

(II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group.

In accordance with a further embodiment, the present invention provides a chirally pure stereoisomer of compound of formula II when $R_2$ is substituted with at least one $NR_3R_4$ group.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" group mean a group consisting of a sulphur atom bonded to an alkyl-, alkenyl- or alkynyl-group, which is bonded via the sulphur atom to the entity to which the group is bonded.

Included within the compounds of the present invention are the tautomeric forms of the disclosed compounds, isomeric forms including diastereoisomers, and the pharmaceutically-acceptable salts thereof.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)-, and individual isomers are encompassed within the scope of the disclosure. The compounds of the present invention do not include those which are known in art to be too unstable to synthesize and/or isolate. The disclosure is meant to include compounds in racemic and optically pure forms in particular attached to the $R_3$ substituent of compound of Formula I. Optically active (R)- and (S)-, isomers may be prepared using chiral synthons or chiral reagents as disclosed herein, or resolved using conventional techniques. When the compounds described herein contain olefinic bonds or other centers of geometric asymmetry, and unless specified otherwise, it is intended that the compounds include both E and Z geometric isomers.

The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

In accordance with one or more of the foregoing embodiments, the present invention provides a compound selected from the group consisting of:

compound 1 (LI-361)

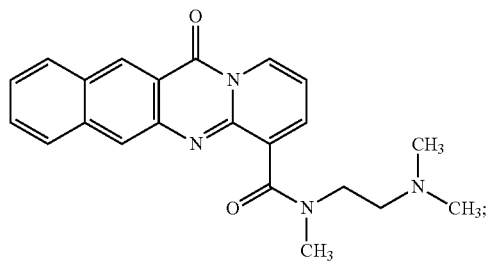

-continued compound 2 (LI-326)

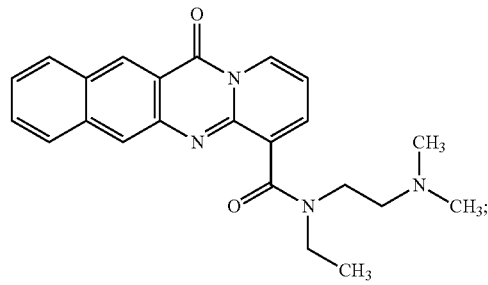

compound 3 (LI-279)

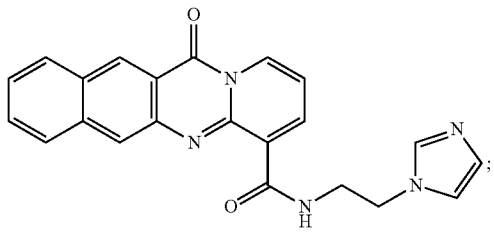

compound 4 (LI-248)

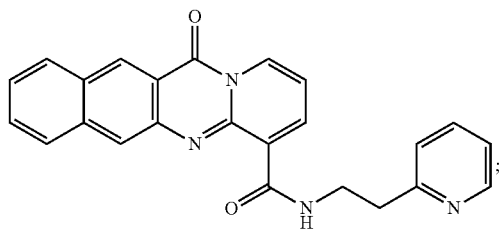

compound 5 (LI-247)

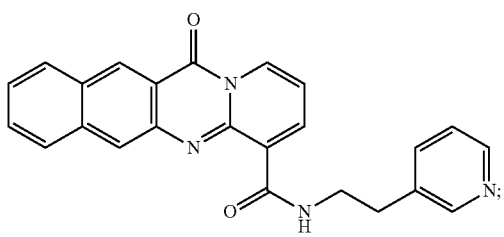

compound 6 (LI-277)

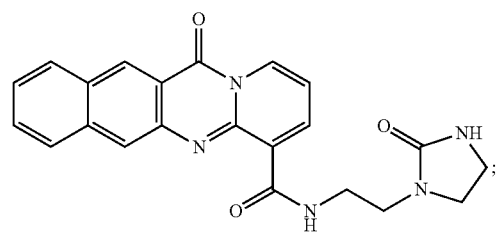

compound 7 (LI-282)

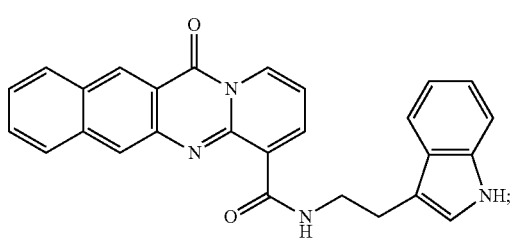

compound 8 (LI-287)
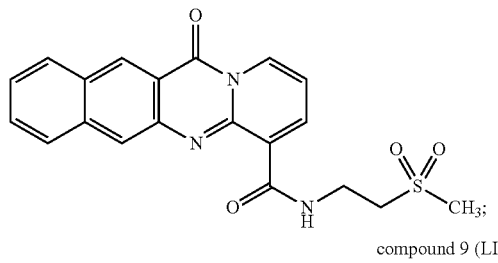
compound 9 (LI-220)
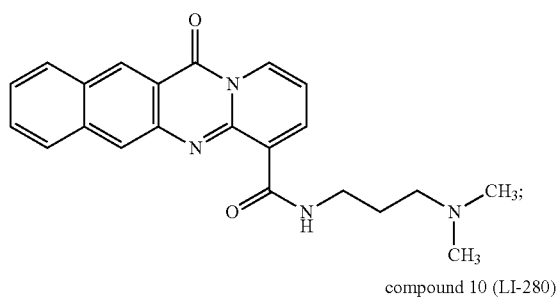
compound 10 (LI-280)
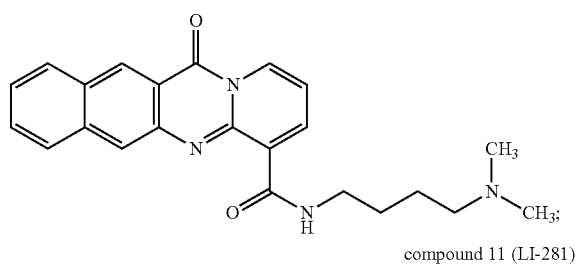
compound 11 (LI-281)
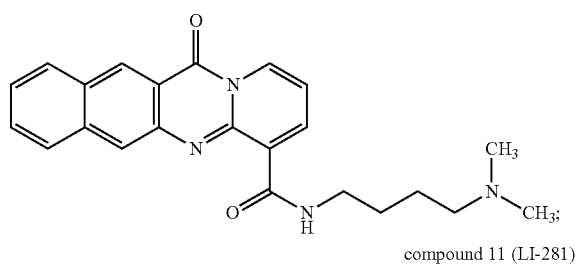
compound 12 (LI-343)
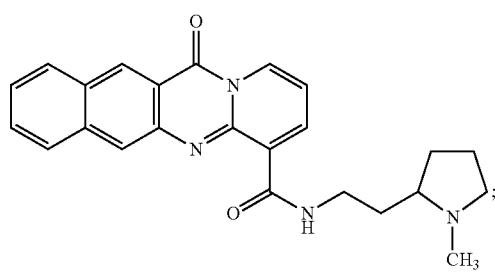
compound 13 (LI-257)
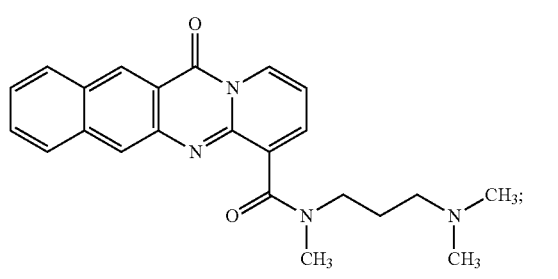
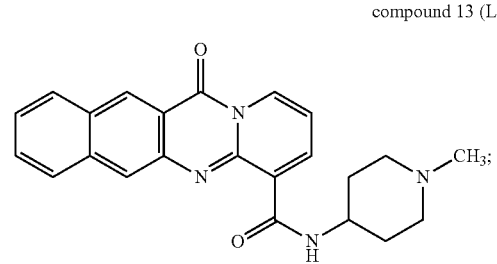
compound 14 (LI-387)
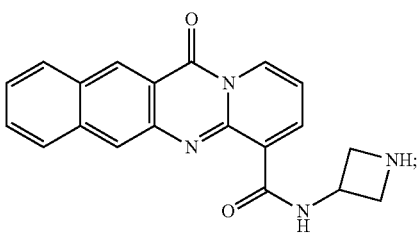
compound 15 (LI-363)
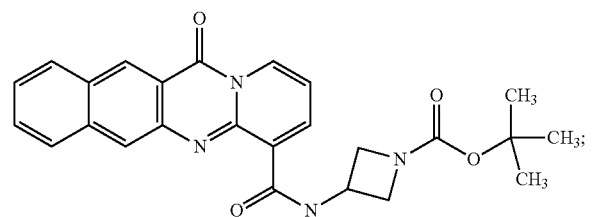
compound 16 (LI-360)
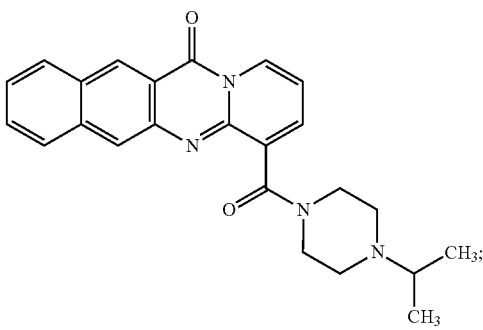
compound 17 (LI-340)
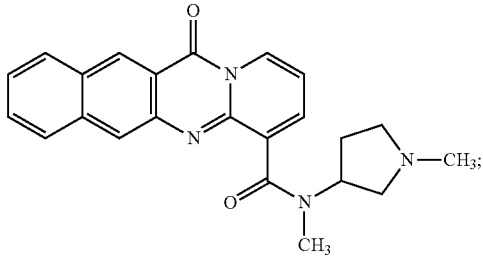
compound 18 (LI-330)
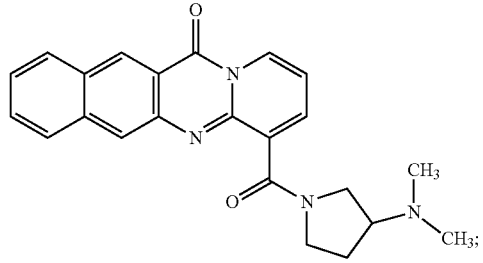

compound 19 (LI-329)
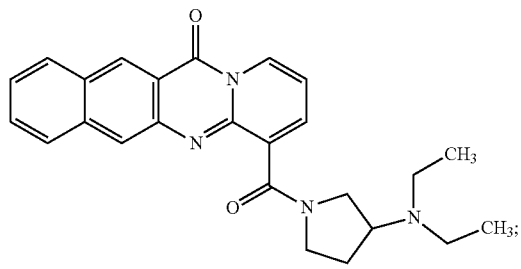
compound 20 (LI-325)
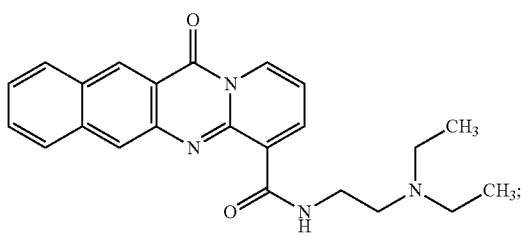
compound 21 (LI-216)
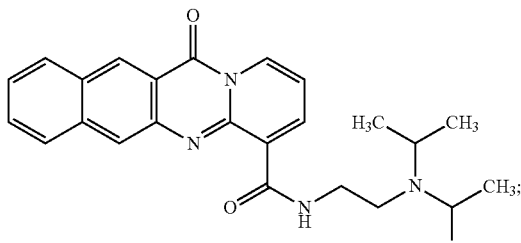
compound 22 (LI-278)
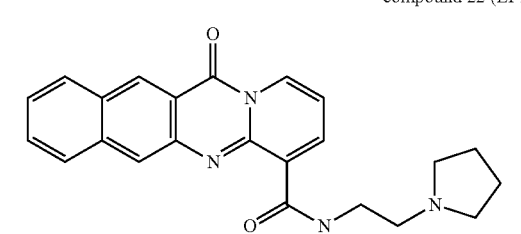
compound 23 (LI-218)
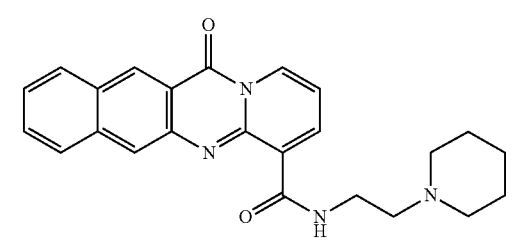
compound 24 (LI-219)
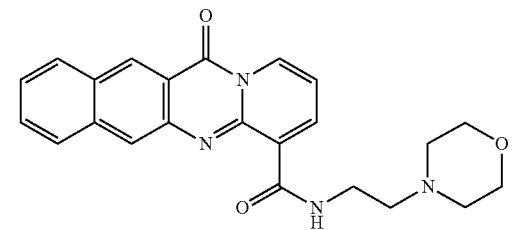
compound 25 (LI-258)
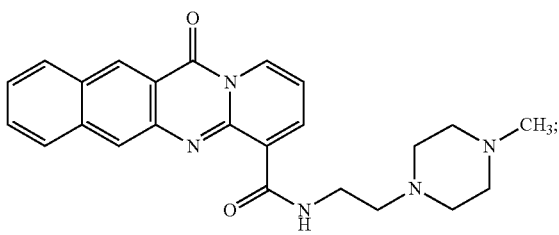
compound 26 (LI-412)
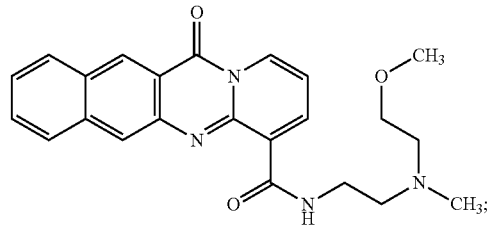
compound 27 (LI-344)
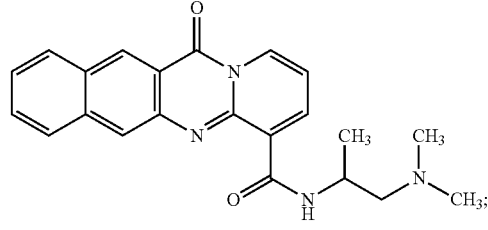
compound 28 (LI-409)
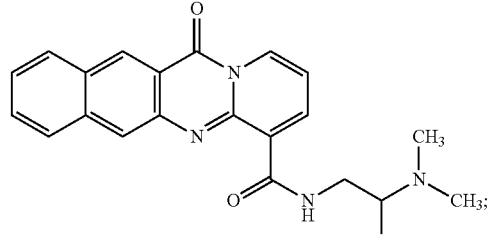
compound 29 (LI-613)
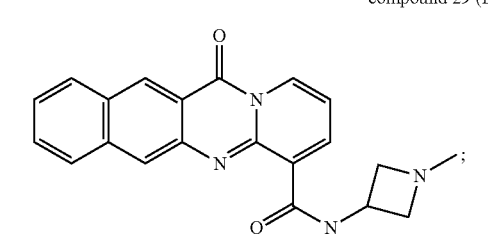
compound 30 (LI-614)
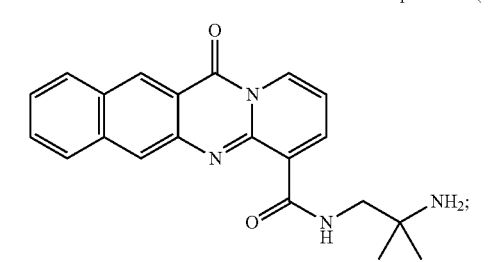

-continued compound 31 (LI-615)

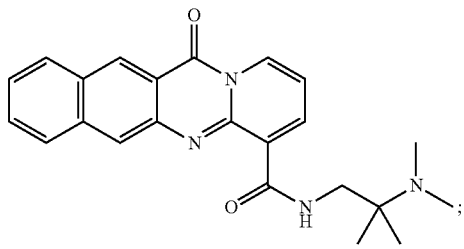

compound 32 (LI-619)

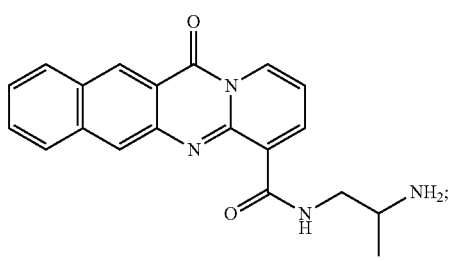

compound 33 (LI-620)

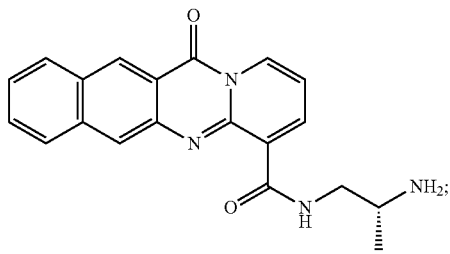

compound 34 (LI-621)

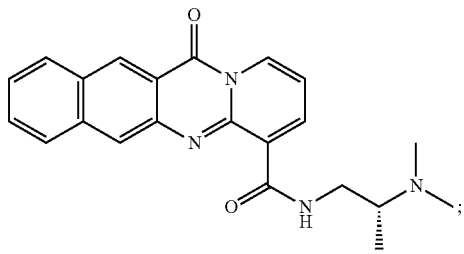

compound 35 (LI-622)

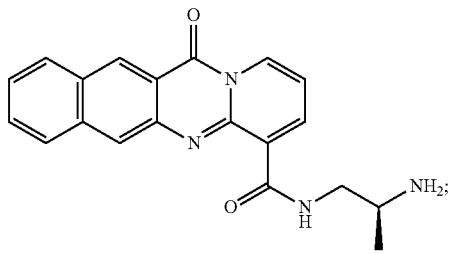

-continued compound 36 (LI-623)

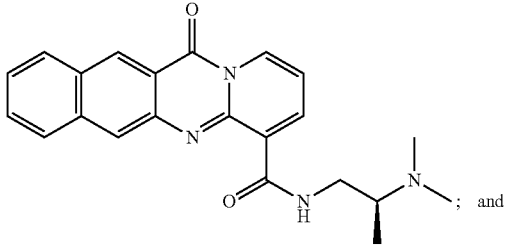; and compound 37 (LI-246)

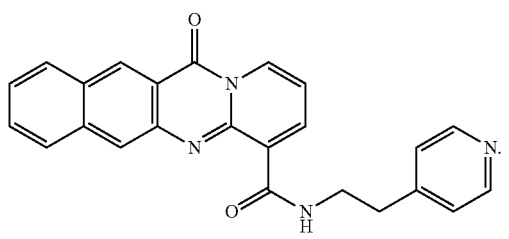

In accordance with an embodiment, the present invention provides pharmaceutical compositions comprising the compounds of formula I, or their salts, solvates, or stereoisomers thereof, and a pharmaceutically acceptable carrier.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As such, in accordance with an embodiment, the present invention provides a pharmaceutical composition comprising the compound of formula I:

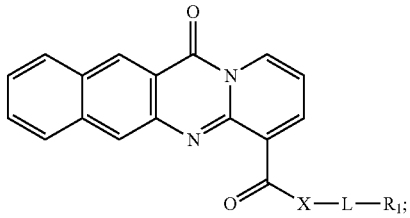

(I)

wherein X is $NR_2$;
wherein L is $R_3$ or an optionally substituted cycloamine

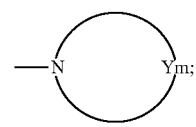

wherein $R_1$ is a straight-chained or branched $C_1$-$C_6$ hydrocarbon group (e.g., an alkyl group, an alkenyl group, an alkynyl group, alkylol group, hydroxyalkyl group, alkoxy group, alkoxyalkyl group, cyclic groups, whether substituted or unsubstituted, such as cyclopentyl, cyclohexyl, pyramido, phenyl, or benzyl, cycloalkyl, heterocyclyl, indole, wherein each of alkyl, aryl, or heterocyclyl moiety may be unsubstituted or substituted with one or more substituents selected from the group consisting of halo, hydroxy, carboxy, phosphoryl, phosphonyl, phosphono $C_1$-$C_6$ alkyl, carboxy $C_1$-$C_6$ alkyl, dicarboxy $C_1$-$C_6$ alkyl, dicarboxy halo $C_1$-$C_6$ alkyl, sulfonyl, cyano, nitro, alkoxy, alkylthio, acyl, acyloxy, thioacyl, acylthio, aryloxy, amino, alkylamino, dialkylamino, trialkylamino, arylalkylamino, guanidino, aldehydo, ureido, and aminocarbonyl, a branched or straight-chain alkylamino, dialkylamino, or alkyl or dialkylaminoalkyl, or thioalkyl, thioalkenyl, thioalkynyl, aryloxy, acyloxy, thioacyl, amido, sulphonamido, etc.), or the like;

when X is $NR_2$, $R_2$ is H or a straight-chained $C_1$-$C_6$ alkyl group;

when L is $R_3$, $R_3$ is a straight-chained or branched $C_2$-$C_6$ alkyl group;

when L is

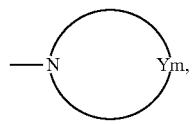

$m=1$-$8$ and each Y is independently selected from $(CH_2)_nY^1_p$ wherein $n=1$-$8$, $p=0$-$4$ and the sum of n and p is at least 2, and each $Y^1$ is independently selected from $NR_4$, O, S, or P, wherein $R_4$ is as hereinbefore defined for $R_3$, and $X \neq O$; or a pharmaceutically acceptable salt, solvate, stereoisomer, or a prodrug thereof, and a pharmaceutically acceptable carrier, in an effective amount, for use as a medicament, preferably for use in inhibiting RNA Pol I in a mammalian cell or population of cells, or for use in treating cancer in a subject.

In accordance with an embodiment, the present invention provides a pharmaceutical composition comprising chirally pure stereoisomer of compound of formula I, wherein L is $R_3$ and $R_3$ is a straight-chained or branched $C_2$-$C_6$ alkyl group having at least one chiral carbon, and a pharmaceutically acceptable carrier. In some embodiments, the pharmaceutical composition can further comprise at least one additional biologically active agent.

In accordance with another embodiment, the present invention provides a pharmaceutical composition comprising compounds of formula II,

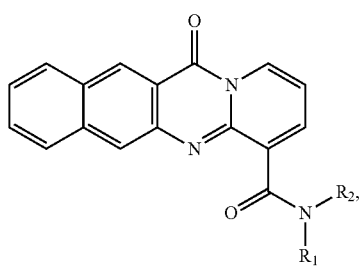

(II)

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, substituted or unsubstituted aryl, substituted or unsubstituted heteroaryl (including but not limited to imidazolyl, imidazolidinonyl, pyridyl, indolyl, oxazolyl, thiazolyl, oxadiazolyl), substituted or unsubstituted cycloalkyl or substituted or unsubstituted nitrogen-containing heterocycles including but not limited to azetidine, pyrrolidine, piperidine, piperazine, azapine, morpholino; wherein $R_3$ and $R_4$, are independently selected from the group including H, $C_1$-$C_6$ alkyl, and $C_1$-$C_4$ alkoxyl alkyl, having at least one chiral carbon, when $R_2$ is substituted with at least one $NR_3R_4$ group.

In accordance with a further embodiment, the present invention provides a pharmaceutical composition comprising a chirally pure stereoisomer of compound of formula II when $R_2$ is substituted with at least one $NR_3R_4$ group and a pharmaceutically acceptable carrier. In some embodiments, the pharmaceutical composition can further comprise at least one additional biologically active agent.

In accordance with another embodiment, the present invention provides a pharmaceutical composition comprising at least one of the compounds selected from the group consisting of:

compound 1 (LI-361)

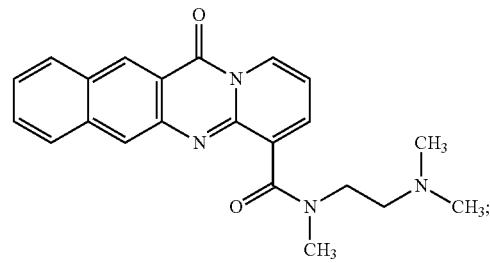

compound 2 (LI-326)

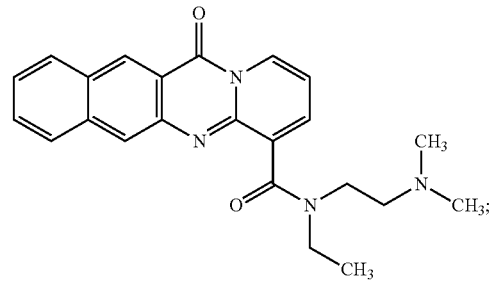

compound 3 (LI-279)

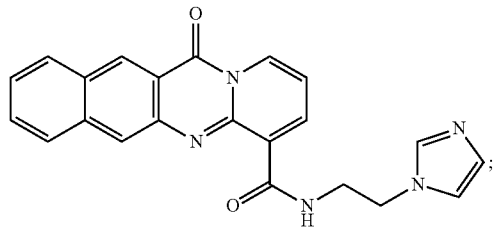

compound 4 (LI-248)

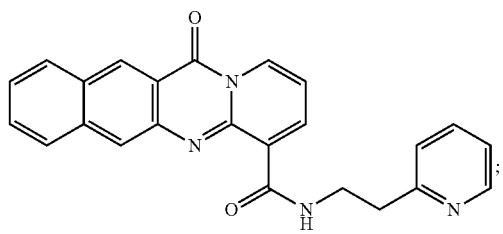

compound 5 (LI-247)
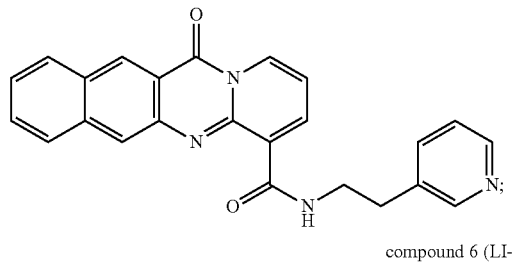
compound 6 (LI-277)
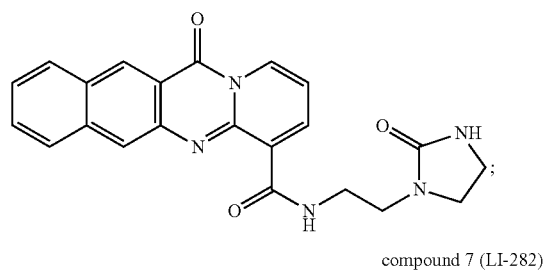
compound 7 (LI-282)
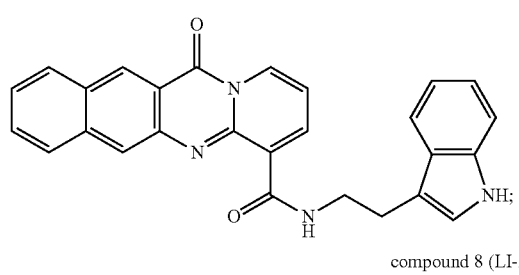
compound 8 (LI-287)
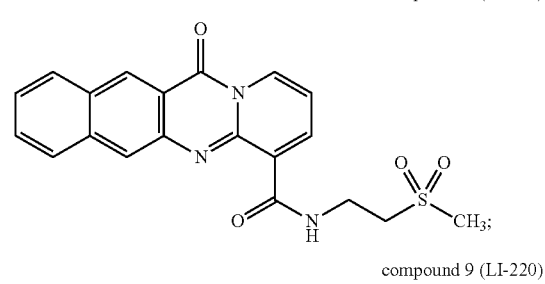
compound 9 (LI-220)
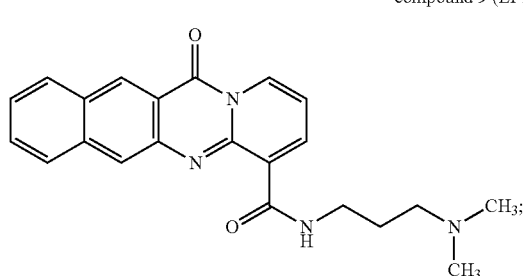
compound 10 (LI-280)
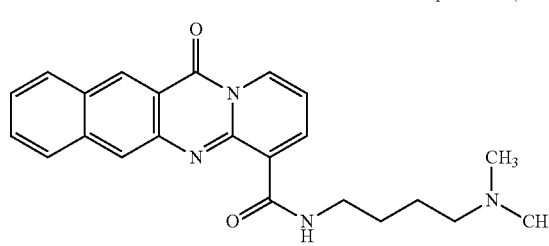
compound 11 (LI-281)
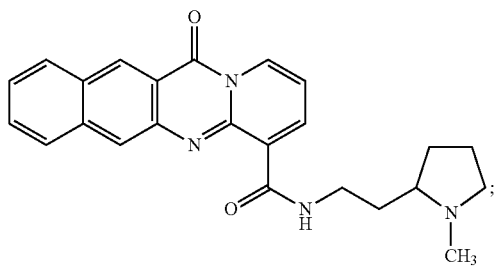
compound 12 (LI-343)
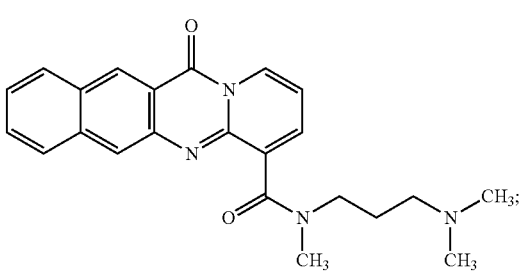
compound 13 (LI-257)
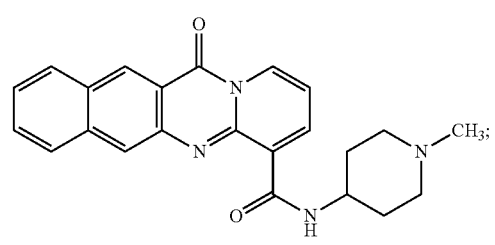
compound 14 (LI-387)
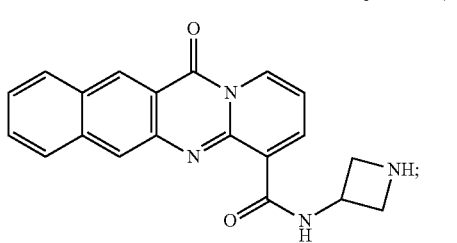
compound 15 (LI-363)
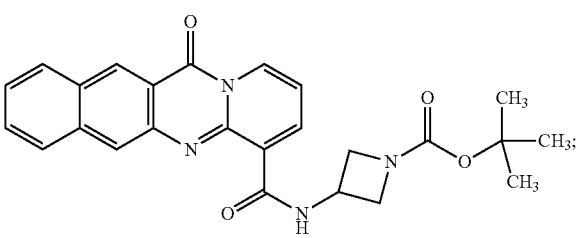

compound 16 (LI-360)
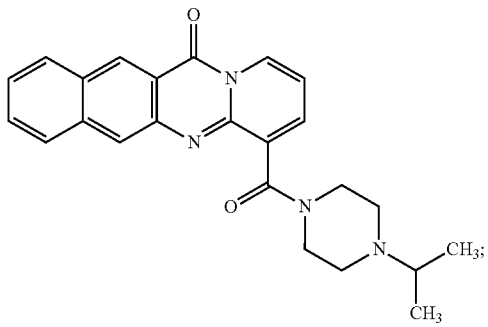
compound 17 (LI-340)
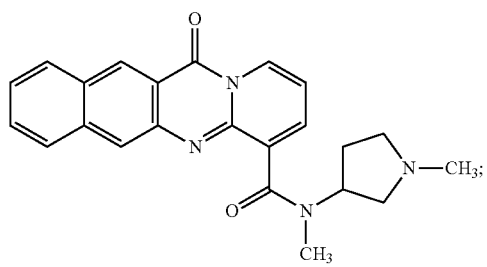
compound 18 (LI-330)
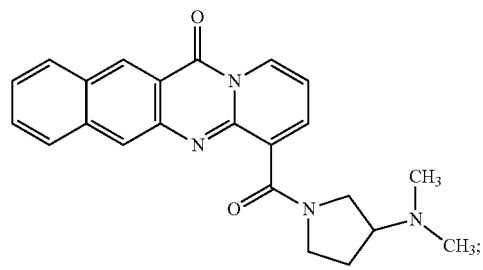
compound 19 (LI-329)
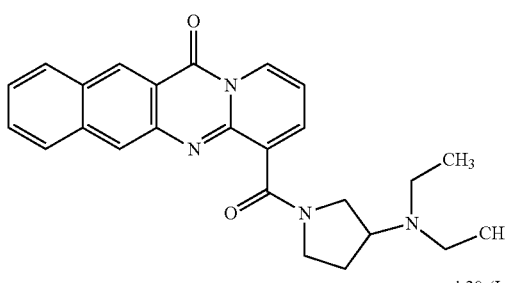
compound 20 (LI-325)
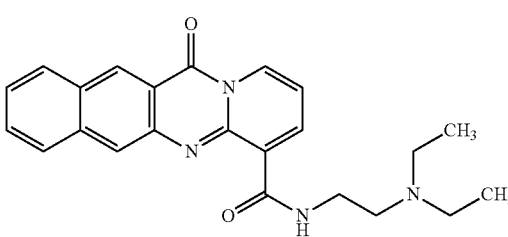
compound 21 (LI-216)
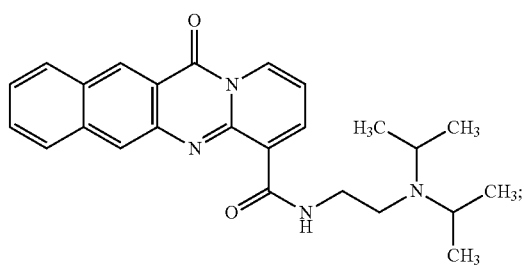
compound 22 (LI-278)
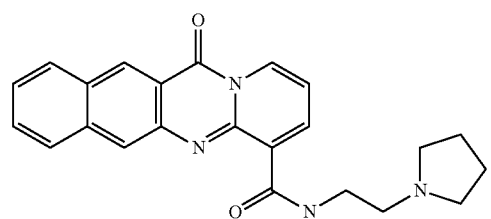
compound 23 (LI-218)
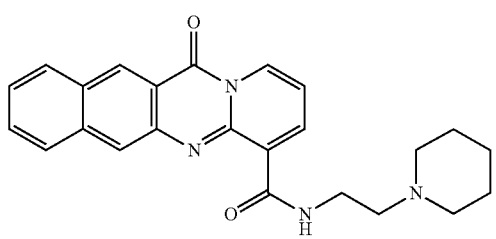
compound 24 (LI-219)
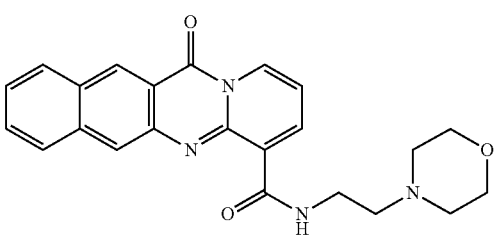
compound 25 (LI-258)
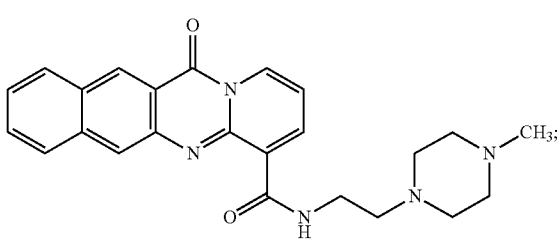
compound 26 (LI-412)
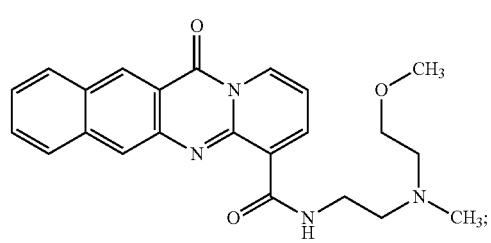

compound 27 (LI-344)

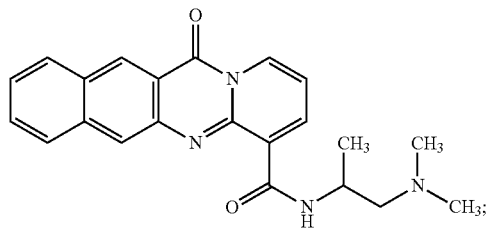

compound 28 (LI-409)

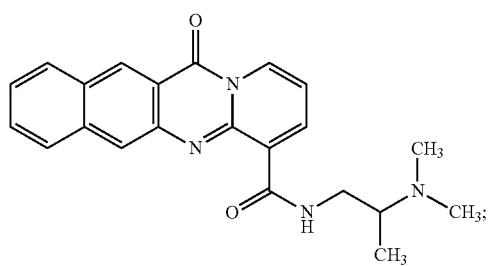

compound 29 (LI-613)

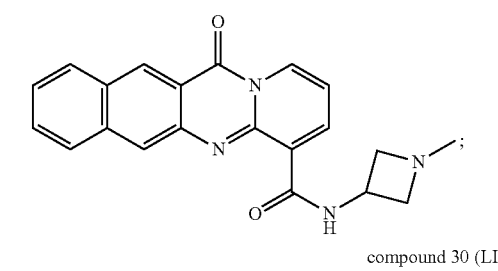

compound 30 (LI-614)

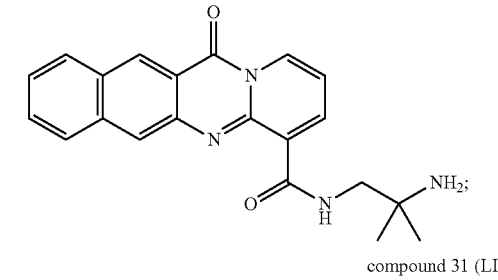

compound 31 (LI-615)

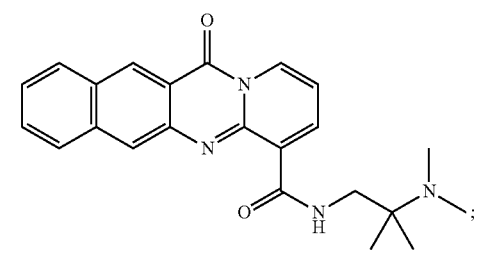

compound 32 (LI-619)

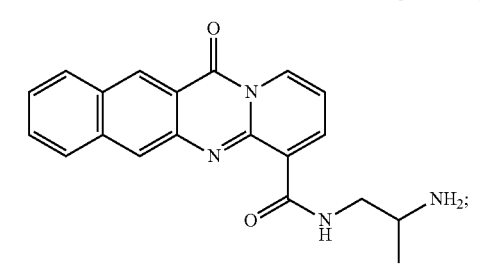

compound 33 (LI-620)

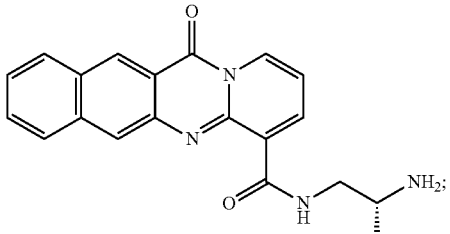

compound 34 (LI-621)

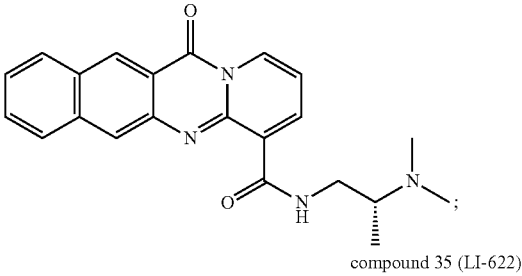

compound 35 (LI-622)

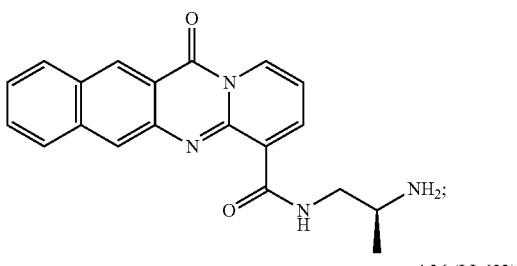

compound 36 (LI-623)

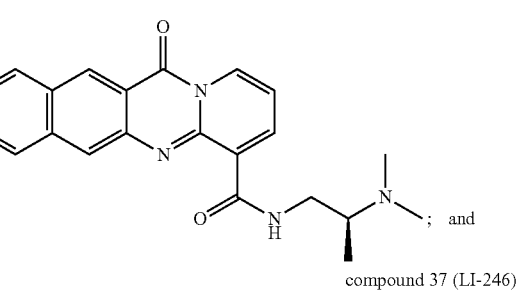

compound 37 (LI-246)

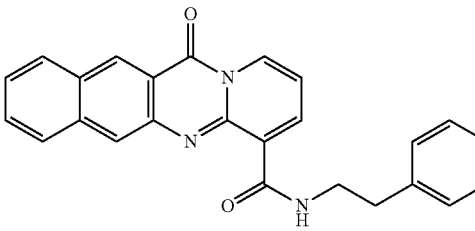

and a pharmaceutically acceptable carrier, in an effective amount, for use as a medicament, preferably for use in inhibiting RNA Pol I in a mammalian cell or population of cells, or for use in treating cancer in a subject.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and*

*Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

It is understood by those of ordinary skill, that the compounds of the present invention are inhibitors of RNA polymerase I through one or more mechanisms of action. Without being limited to any particular theory, the compounds of the present invention can inhibit RNA Pol I by intercalation of the nucleic acids at G-C rich regions which block the polymerase activity.

One of ordinary skill in the art understands that p53 is a highly responsive molecule to cellular stress and DNA damage, and implicated in diverse diseases like cancer, ischemia, neuronal disorders, inflammation and also during physiological processes like in normal cellular metabolism, development and aging. Thus, the compounds of the present invention are useful in prevention or treatment of diseases involving the p53 pathways.

Therefore, in accordance with an embodiment, the present invention provides the use of the compounds or the pharmaceutical compositions disclosed herein in an amount effective for activating upstream p53 pathways in a mammalian cell comprising contacting a cell or population of cells with a compound of formula I.

In accordance with an embodiment, the present invention provides the use of the compounds or the pharmaceutical compositions disclosed herein in an amount effective for modulating RNA Pol I activity in a mammalian cell comprising contacting a cell or population of cells with a compound of formula I.

In accordance with an embodiment, the present invention provides the use of the compounds or the pharmaceutical compositions disclosed herein in an amount effective for treating cancer or a hyperproliferative disease in a subject comprising administering to the subject a pharmaceutical composition comprising a compound of formula I. In an alternative embodiment, the use includes at least one additional biologically active agent.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, or from about 1 mg to about 100 mg/kg body weight/day. In some embodiments the dosage of the compound can be in the range of about 0.1 μM to about 100 μM, preferably about 1 μM to about 50 μM.

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all, or substantially all of the compound, is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

An active agent and a biologically active agent are used interchangeably herein to refer to a chemical or biological compound that induces a desired pharmacological and/or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like. When the terms "active agent," "pharmacologically active agent" and "drug" are used, then, it is to be understood that the invention includes the active agent per se as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

Further examples of biologically active agents include, without limitation, enzymes, receptor antagonists or agonists, hormones, growth factors, autogenous bone marrow, antibiotics, antimicrobial agents, RNA and DNA molecules and nucleic acids, and antibodies. Specific examples of useful biologically active agents the above categories include: anti-neoplastics such as androgen inhibitors, antimetabolites, cytotoxic agents, and immunomodulators.

Biologically active agents also include anti-cancer agents such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics.

Further examples of alkylating antineoplastic agents include carboplatin and cisplatin; nitrosourea alkylating antineoplastic agents, such as carmustine (BCNU); antimetabolite antineoplastic agents, such as methotrexate; pyrimidine analog antineoplastic agents, such as fluorouracil (5-FU) and gemcitabine; hormonal antineoplastics, such as goserelin, leuprolide, and tamoxifen; natural antineoplastics, such as aldesleukin, interleukin-2, docetaxel, etoposide, interferon; paclitaxel, other taxane derivatives, and tretinoin (ATRA); antibiotic natural antineoplastics, such as bleomycin, dactinomycin, daunorubicin, doxorubicin, and mitomycin; vinca alkaloid natural antineoplastics, such as vinblastine and vincristine, and PD 1 inhibitors such as lambrolizumab.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

As used herein, the term "modulate" means that the compounds of formula I, described herein either increase or decrease the activity of RNA Pol I.

As used herein, the term "hyperproliferative disease" includes cancer and other diseases such as neoplasias and hyperplasias. Cellular proliferative diseases include, for example, rheumatoid arthritis, inflammatory bowel disease, osteoarthritis, leiomyomas, adenomas, lipomas, hemangiomas, fibromas, vascular occlusion, restenosis, artherosclerosis, a pre-neoplastic lesion, carcinoma in situ, oral hairy leukoplakia, or psoriasis. In accordance with one or more embodiments, the term cancer can include any of acute lymphocytic cancer, acute myeloid leukemia, alveolar rhabdomyosarcoma, bone cancer, brain cancer, central nervous system cancer, peripheral nerve sheet tumors, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

EXAMPLES

Cells and Viability Assay. The cells were maintained at 37° C. in a humidified atmosphere containing 5% $CO_2$. U2OS ostesarcoma cells were cultured in DMEM supplemented with 15% fetal bovine serum. Cells were plated in 96-well plates at a density of 10,000 cells/well in triplicate and incubated for 48 hours with the compounds. Viability was determined using WST-1 cell proliferation reagent (Roche Diagnostics).

Immunofluorescence, Epifluorescence Microscopy and Image Analysis. U2OS cells grown on coverslips were fixed in 3.5% paraformaldehyde, permeabilized with 0.5% NP-40 and blocked with 3% BSA as described in Peltonen et al (Mol. Cancer Ther. 2014). Cells were stained for RPA194 (C-1, Santa Cruz Biotechnology) and NCL (4E2, Abeam). Alexa 488 and Alexa 594-conjugated anti-mouse or anti-rabbit antibodies were from Invitrogen. DNA was counterstained with DAPI (Invitrogen). Images were captured using Axioplan2 fluorescence microscope (Zeiss) equipped with AxioCam HRc CCD-camera and AxioVision 4.5 software using EC Plan-Neofluar 20×/0.75 objective (Zeiss). Images were quantified using FrIDA image analysis software as described in Peltonen et al. (2014). Hue saturation and brightness range were defined individually for RPA194 and NCL. All values were normalized to the DNA content. Two-four fields of each treatment were recorded and quantification was based on an average of 200 cells.

Immunoblotting. Lysis of cells was conducted in 0.5% NP-40 buffer (25 mM Tris-HCl, pH 8.0, 120 mM NaCl, 0.5% NP-40, 4 mM NaF, 100 µM $Na_3VO_4$, 100 KIU/mL aprotinin, 10 µg/mL leupeptin). Proteins were separated on SDS-PAGE gel and blotted as in (Peltonen et al. 2010). The following antibodies were used: NCL (4E2, Abeam), RPA194 (C-1, Santa Cruz Biotechnology), GAPDH (Europa Bioproducts). HRP-conjugated secondary antibodies were from DAKO.

Determination of RPA194 and NCL $IC_{50}$. U2OS cells grown on coverslips were treated the compounds at 0.1, 0.5, 1, 5 and 10 µM, or vehicle (DMSO)-treated for 3 h and fixed and stained as above. All compounds, except when indicated, were tested in duplicate independent biological experiments Immunostaining for NCL and RPA194 was conducted separately, and cells were counterstained for DNA. Two-four fields of each treatment were captured using epifluorescence microscopy as above, and contained on average of 200 cells/analysis. The images were quantified using FrIDA image analysis software as described in ref 14. Hue saturation and brightness range were defined individually for RPA194 and NCL, and all values were normalized to the DNA content. The fold change to control was determined $IC_{50}$ was determined by GraphPad Prism for Windows (version 6.01) using a three-parameter fit.

Synthesis. General Methods. All commercially available reagents and solvents were used without further purification unless otherwise stated. Automated flash chromatography was performed on an ISCO CombiFlash Rf or Biotage Isolera using Biotage Flash cartridges with peak detection at 254 nm. Reverse phase purification was accomplished using a Gilson 215 liquid handler equipped with a Phenomenex C18 column (150×20 mm I.D., S-5 μm). Peak collection was triggered by UV detection at 214 or 254 nm. $^1$H NMR spectra were recorded on a Bruker 400 instrument operating at 400 MHz with tetramethylsilane or residual protonated solvent used as a reference. Analytical LC/MS was performed using Agilent 1260 equipped with autosampler (Agilent Poroshell 120 C18 column (50×4.6 mm I.D., 3.5 μm); 0.1% TFA in water/acetonitrile gradient; UV detection at 215 and 254 nm) and electrospray ionization.

The general synthetic scheme:

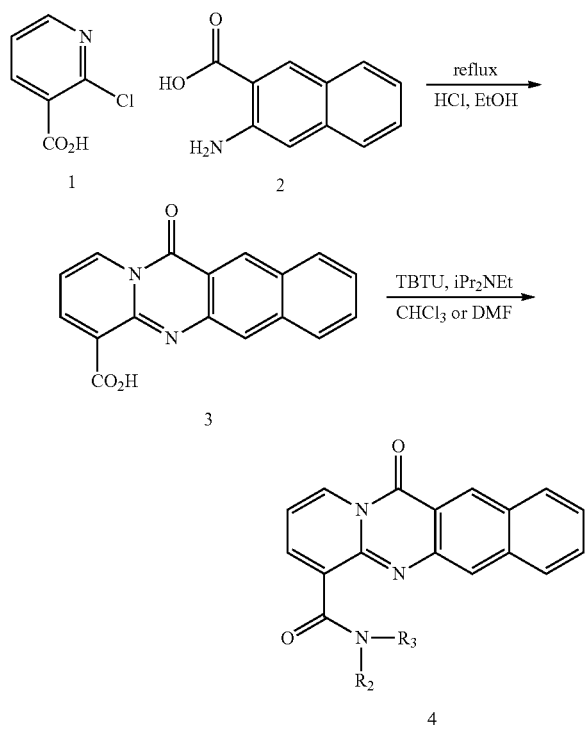

12-oxo-12H-benzo[g]pyrido[2,1-b]quinazoline-4-carboxylic acid (3a)

A mixture of 3-amino-2-naphthoic acid (2) (2.00 g, 10.68 mmol), 2-chloronicotinic acid (1) (1.68 g, 10.68 mmol) and hydrochloric acid (0.9 mL, 29.13 mmol) in ethanol (70 mL) were stirred at 80° C. for 66 h (for convenience). After cooling, the reddish-orange suspension was filtered, washed with ethanol and air-dried to give 12-oxo-12H-benzo[g]pyrido[2,1-b]quinazoline-4-carboxylic acid (1.56 g, 5.37 mmol, 50.3% yield) as a yellow-orange solid. $^1$H NMR (400 MHz, DMSO-$d_6$) δ ppm 9.16 (s, 1H) 9.03 (dd, J=7.20, 1.64 Hz, 1H) 8.63 (dd, J=6.95, 1.64 Hz, 1H) 8.49 (s, 1H) 8.34 (d, J=8.34 Hz, 1H) 8.19 (d, J=8.08 Hz, 1H) 7.76 (t, J=7.07 Hz, 1H) 7.64 (t, J=6.95 Hz, 1H) 7.18 (t, J=7.07 Hz, 1H). MS [M+1]=291.

11-oxopyrido[2,1-b]quinazoline-6-carboxylic acid (3b)

A mixture of 2-aminobenzoic acid (250 mg, 1.82 mmol), 2-chloronicotinic acid (287.2 mg, 1.82 mmol) and hydrochloric acid (0.3 mL, 9.85 mmol) in ethanol (20 mL) were stirred at 80° C. for 48 h (for convenience). After cooling, the reddish-orange suspension was filtered, washed with ethanol and air-dried to give 11-oxopyrido[2,1-b]quinazoline-6-carboxylic acid (107 mg, 0.45 mmol, 24.5% yield) as a pale yellow solid. $^1$H NMR (400 MHz, CDCl$_3$) δ ppm 9.50 (dd, J=7.07, 1.52 Hz, 3H) 9.18 (dd, J=7.45, 1.64 Hz, 3H) 8.56 (dd, J=8.21, 1.39 Hz, 3H) 8.17 (ddd, J=8.46, 7.20, 1.52 Hz, 3H) 8.03 (s, 2H) 8.01 (s, 1H) 7.80 (ddd, J=8.15, 7.26, 1.01 Hz, 4H) 7.72 (t, J=7.20 Hz, 3H). MS [M+1]=241.

Method A: Synthesis of amide analogues (4). N-[2-(dimethylamino)ethyl]-12-oxo-12H-benzo[g]pyrido[2,1-b]quinazoline-4-carboxamide. To a solution of 12-oxo-12H-benzo[g]pyrido[2,1-b]quinazoline-4-carboxylic acid (50.mg, 0.17 mmol) and TBTU (82.9 mg, 0.26 mmol) in DMF (1 mL) was added DIPEA (90 μL, 0.52 mmol). After the contents were stirred at room temperature for 15 minutes, N,N-dimethylethylenediamine (28.4 μL, 0.26 mmol) was added, and stirring continued for 16 hours (for convenience). Added reaction mixture to 100 mL cold water with stirring. Collected solid by filtration and dried under vacuum to give N-[2-(dimethylamino)ethyl]-12-oxo-12H-benzo[g]pyrido[2,1-b]quinazoline-4-carboxamide (36 mg, 0.10 mmol, 58.0% yield) as a yellow solid. 1H NMR (400 MHz, DMSO-d6) δ ppm 11.50 (br. s., 1H) 9.10 (s, 1H) 8.91 (d, J=5.81 Hz, 1H) 8.55 (d, J=5.56 Hz, 1H) 8.28-8.34 (m, 2H) 8.12 (d, J=8.34 Hz, 1H) 7.73 (t, J=7.45 Hz, 1H) 7.61 (t, J=7.33 Hz, 1H) 7.05 (t, J=7.07 Hz, 1H) 3.56 (d, J=5.05 Hz, 2H) 2.59 (t, J=5.94 Hz, 2H) 2.40 (s, 6H). 1H NMR (400 MHz, CDCl3) δ ppm 11.70 (br. s., 1H) 9.10 (s, 1H) 8.94 (dd, J=7.33, 1.77 Hz, 1H) 8.73 (dd, J=6.82, 1.77 Hz, 1H) 8.29 (s, 1H) 8.12 (d, J=8.59 Hz, 1H) 8.00 (d, J=8.34 Hz, 1H) 7.66 (t, J=7.58 Hz, 1H) 7.52-7.60 (m, 1H) 6.89 (t, J=7.07 Hz, 1H) 3.66-3.77 (m, 2H) 2.71 (t, J=6.06 Hz, 2H) 2.49 (s, 6H). MS [M+1]=361.

Example 1

N-[2-(dimethylamino)ethyl]-N-methyl-12-oxo-12H-benzo[g]pyrido[2,1-b]quinazoline-4-carboxamide (compound 1)

This compound was synthesized from 3a (50 mg, 0.17 mmol) and N,N,N'-trimethylethylenediamine (21.3 μL, 0.17 mmol) according to Method A to give N-[2-(dimethylamino)ethyl]-N-methyl-12-oxo-12H-benzo[g]pyrido[2,1-b]quinazoline-4-carboxamide trifluoroacetate (18.8 mg, 0.050 mmol, 29.1% yield) as an orange solid. $^1$H NMR (400 MHz, CDCl$_3$) δ ppm 9.14 (s, 1H) 8.93 (d, J=7.33 Hz, 1H) 8.28 (s, 1H) 8.14 (d, J=8.34 Hz, 1H) 8.04 (d, J=8.84 Hz, 1H) 7.93 (d, J=6.82 Hz, 1H) 7.67-7.74 (m, 1H) 7.58-7.64 (m, 1H) 6.97 (t, J=7.07 Hz, 1H) 4.12 (t, J=5.94 Hz, 2H) 3.57 (t, J=6.19 Hz, 2H) 3.12 (s, 6H) 3.10 (s, 3H). MS [M+1]=375.

Example 2

N-[2-(dimethylamino)ethyl]-N-ethyl-12-oxo-12H-benzo[g]pyrido[2,1-b]quinazoline-4-carboxamide (compound 2)

This compound was synthesized from 3a (50 mg, 0.17 mmol) and N,N-dimethyl-N'-ethylethylenediamine (27.1

µL, 0.17 mmol) according to Method A to give N-[2-(dimethylamino)ethyl]-N-ethyl-12-oxo-12H-benzo[g]pyrido[2,1-b]quinazoline-4-carboxamide trifluoroacetate (36.1 mg, 0.093 mmol, 54% yield) as a yellow-orange solid. $^1$H NMR (400 MHz, CDCl$_3$) δ ppm 9.13 (s, 1H) 8.87 (d, J=7.33 Hz, 1H) 8.21 (s, 1H) 8.13 (d, J=8.34 Hz, 1H) 8.03 (d, J=8.59 Hz, 1H) 7.65-7.71 (m, 1H) 7.56-7.62 (m, 2H) 6.84 (t, J=7.07 Hz, 1H) 4.06 (m, 2H) 3.62 (t, J=6.69 Hz, 2H) 3.39 (q, J=7.24 Hz, 2H) 3.12 (s, 6H) 1.20 (t, J=7.07 Hz, 3H). MS [M+1]=389.

Example 3

N-(2-imidazol-1-ylethyl)-12-oxo-12H-benzo[g]pyrido[2,1-b]quinazoline-4-carboxamide (compound 3)

This compound was synthesized from 3a (50 mg, 0.17 mmol) and 2-imidazol-1-ylethanamine (16.6 µL, 0.17 mmol) according to Method A to give N-(2-imidazol-1-ylethyl)-12-oxo-12H-benzo[g]pyrido[2,1-b]quinazoline-4-carboxamide (28.5 mg, 0.074 mmol, 43% yield) as a yellow-orange solid. $^1$H NMR (400 MHz, CDCl$_3$) δ ppm 11.57 (br. s., 1H) 9.08 (s, 1H) 8.98 (dd, J=7.07, 1.77 Hz, 1H) 8.73 (dd, J=7.07, 1.77 Hz, 1H) 8.10 (t, J=8.34 Hz, 3H) 7.94 (s, 1H) 7.66-7.72 (m, 3H) 7.55-7.60 (m, 2H) 7.22 (s, 1H) 7.16 (s, 1H) 6.91 (t, J=7.07 Hz, 2H) 4.32-4.37 (m, 2H) 4.01-4.07 (m, 2H). MS [M+1]=384.

Example 4

12-oxo-N-[2-(2-pyridyl)ethyl]-12H-benzo[g]pyrido[2,1-b]quinazoline-4-carboxamide (compound 4)

This compound was synthesized from 3a (50 mg, 0.17 mmol) and 2-(2-aminoethyl)pyridine (20.6 µL, 0.17 mmol) according to Method A to give 12-oxo-N-[2-(2-pyridyl)ethyl]-12H-benzo[g]pyrido[2,1-b]quinazoline-4-carboxamide (40.7 mg, 0.103 mmol, 60% yield) as an orange solid. $^1$H NMR (400 MHz, DMSO-d$_6$) δ ppm 11.39 (br. s., 1H) 9.12 (s, 1H) 8.96 (dd, J=7.33, 1.77 Hz, 1H) 8.75 (dd, J=7.07, 1.77 Hz, 1H) 8.26 (s, 1H) 8.13 (d, J=8.59 Hz, 1H) 8.03 (d, J=8.59 Hz, 1H) 7.64-7.72 (m, 1H) 7.53-7.61 (m, 1H) 6.91 (t, J=7.07 Hz, 1H) 3.64-3.74 (m, 2H) 2.50-2.58 (m, 2H). MS [M+1]=395.

Example 5

12-oxo-N-[2-(3-pyridyl)ethyl]-12H-benzo[g]pyrido[2,1-b]quinazoline-4-carboxamide (compound 5)

This compound was synthesized from 3a (50 mg, 0.17 mmol) and 3-(2-aminoethyl)pyridine (20.5 µL, 0.17 mmol) according to Method A to give 12-oxo-N-[2-(3-pyridyl)ethyl]-12H-benzo[g]pyrido[2,1-b]quinazoline-4-carboxamide (55 mg, 0.14 mmol, 81% yield) as an orange solid. $^1$H NMR (400 MHz, DMSO-d$_6$) δ ppm 11.39 (br. s., 1H) 9.12 (s, 1H) 8.96 (dd, J=7.33, 1.77 Hz, 1H) 8.75 (dd, J=7.07, 1.77 Hz, 1H) 8.26 (s, 1H) 8.13 (d, J=8.59 Hz, 1H) 8.03 (d, J=8.59 Hz, 1H) 7.64-7.72 (m, 1H) 7.53-7.61 (m, 1H) 6.91 (t, J=7.07 Hz, 1H) 3.64-3.74 (m, 2H) 2.50-2.58 (m, 2H). MS [M+1]=395.

Example 6

12-oxo-N-[2-(2-oxoimidazolidin-1-yl)ethyl]-12H-benzo[g]pyrido[2,1-b]quinazoline-4-carboxamide (compound 6)

This compound was synthesized from 3a (50 mg, 0.17 mmol) and 1-(2-aminoethyl)imidazolidin-2-one (19.6 µL, 0.17 mmol) according to Method A to give 12-oxo-N-[2-(2-oxoimidazolidin-1-yl)ethyl]-12H-benzo[g]pyrido[2,1-b]quinazoline-4-carboxamide (6.5 mg, 0.016 mmol, 9.4% yield) as a yellow-orange solid. $^1$H NMR (400 MHz, CDCl$_3$) δ ppm 11.54 (br. s., 1H) 9.12 (s, 1H) 8.98 (dd, J=7.20, 1.64 Hz, 1H) 8.74 (d, J=7.07 Hz, 1H) 8.43 (s, 1H) 8.12 (dd, J=12.63, 8.08 Hz, 2H) 7.66-7.71 (m, 1H) 7.57 (dd, J=15.79, 8.72 Hz, 2H) 7.02 (s, 1H) 6.91 (t, J=7.33 Hz, 1H) 3.80-3.88 (m, 2H) 3.61-3.69 (m, 4H) 3.47 (m, 2H). MS [M+1]=402.

Example 7

N-[2-(1H-indol-3-yl)ethyl]-12-oxo-12H-benzo[g]pyrido[2,1-b]quinazoline-4-carboxamide (compound 7)

This compound was synthesized from 3a (50 mg, 0.17 mmol) and tryptamine (27.6 mg, 0.17 mmol) according to Method A to give N-[2-(1H-indol-3-yl)ethyl]-12-oxo-12H-benzo[g]pyrido[2,1-b]quinazoline-4-carboxamide (22.9 mg, 0.053 mmol, 30.7% yield) as a yellow-orange solid. $^1$H NMR (400 MHz, CDCl$_3$) δ ppm 11.43-11.50 (m, 1H) 9.04 (s, 1H) 8.91-8.95 (m, 1H) 8.77 (dd, J=6.82, 1.77 Hz, 1H) 8.06 (s, 2H) 7.83 (d, J=7.33 Hz, 1H) 7.74 (d, J=8.08 Hz, 1H) 7.60-7.67 (m, 1H) 7.54 (s, 1H) 7.47 (s, 1H) 7.34 (s, 2H) 7.19-7.26 (m, 3H) 7.16 (d, J=2.02 Hz, 2H) 6.90 (t, J=7.20 Hz, 1H) 4.08 (d, J=6.06 Hz, 2H) 3.27 (m, 2H). MS [M+1]=433.

Example 8

N-(2-methylsulfonylethyl)-12-oxo-12H-benzo[g]pyrido[2,1-b]quinazoline-4-carboxamide (compound 8)

This compound was synthesized from 3a (50 mg, 0.17 mmol) and 2-methylsulfonylethanamine (21.2 mg, 0.17 mmol) according to Method A to give N-(2-methylsulfonylethyl)-12-oxo-12H-benzo[g]pyrido[2,1-b]quinazoline-4-carboxamide (2.1 mg, 0.0053 mmol, 3.1% yield) as a yellow-orange solid. $^1$H NMR (400 MHz, CDCl$_3$) δ ppm 11.93 (br. s., 1H) 9.12 (s, 1H) 9.00 (dd, J=7.45, 1.64 Hz, 1H) 8.73 (dd, J=6.95, 1.64 Hz, 1H) 8.49 (s, 1H) 8.12 (t, J=8.84 Hz, 2H) 7.67-7.72 (m, 1H) 7.56-7.62 (m, 1H) 6.92 (t, J=7.07 Hz, 1H) 4.16-4.22 (m, 2H) 3.49-3.54 (m, 2H) 3.07 (s, 3H). MS [M+1]=396.

Example 9

N-[3-(dimethylamino)propyl]-12-oxo-12H-benzo[g]pyrido[2,1-b]quinazoline-4-carboxamide (compound 9)

This compound was synthesized from 3a (50 mg, 0.17 mmol) and N,N-dimethyl-1,3-propanediamine (21.7 µL, 0.17 mmol) according to Method A to give N-[3-(dimethylamino)propyl]-12-oxo-12H-benzo[g]pyrido[2,1-b]quinazoline-4-carboxamide (18.1 mg, 0.048 mmol, 28.1% yield) as an orange solid. $^1$H NMR (400 MHz, DMSO-d$_6$) δ ppm 11.39 (br. s., 1H) 9.12 (s, 1H) 8.96 (dd, J=7.33, 1.77 Hz, 1H) 8.75 (dd, J=7.07, 1.77 Hz, 1H) 8.26 (s, 1H) 8.13 (d, J=8.59 Hz, 1H) 8.03 (d, J=8.59 Hz, 1H) 7.64-7.72 (m, 1H) 7.53-7.61 (m, 1H) 6.91 (t, J=7.07 Hz, 1H) 3.64-3.74 (m, 2H) 2.50-2.58 (m, 2H) 2.33 (s, 6H) 1.98 (quin, J=7.14 Hz, 2H). MS [M+1]=375.

Example 10

N-[4-(dimethylamino)butyl]-12-oxo-12H-benzo[g]pyrido[2,1-b]quinazoline-4-carboxamide (compound 10)

This compound was synthesized from 3a (50 mg, 0.17 mmol) and N',N'-dimethylbutane-1,4-diamine (24.5 µL, 0.17 mmol) according to Method A to give N-[4-(dimethylamino)butyl]-12-oxo-12H-benzo[g]pyrido[2,1-b]quinazoline-4-carboxamide (22.1 mg, 0.057 mmol, 33% yield) as a yellow-orange solid. $^1$H NMR (400 MHz, CDCl$_3$) δ ppm 11.35-11.41 (m, 1H) 9.13 (s, 1H) 8.98 (dd, J=7.20, 1.64 Hz, 1H) 8.76 (dd, J=6.95, 1.64 Hz, 1H) 8.26 (s, 1H) 8.14 (d, J=8.59 Hz, 1H) 8.06 (d, J=8.59 Hz, 1H) 7.66-7.72 (m, 1H) 7.54-7.63 (m, 1H) 6.92 (t, J=7.07 Hz, 1H) 3.62-3.73 (m, 2H) 2.46-2.52 (m, 2H) 2.32 (s, 6H) 1.59-1.91 (m, 4H). MS [M+1]=389.

Example 11

N-[2-(1-methylpyrrolidin-2-yl)ethyl]-12-oxo-12H-benzo[g]pyrido[2,1-b]quinazoline-4-carboxamide (compound 11)

This compound was synthesized from 3a (50 mg, 0.17 mmol) and 2-(2-aminoethyl)-1-methylpyrrolidine (22 mg, 25 µL, 0.17 mmol) according to Method A to give N-[2-(1-methylpyrrolidin-2-yl)ethyl]-12-oxo-12H-benzo[g]pyrido[2,1-b]quinazoline-4-carboxamide (18 mg, 0.045 mmol, 26% yield) as a yellow-orange solid. $^1$H NMR (400 MHz, CDCl$_3$) δ ppm 11.59 (br. s., 1H) 9.10 (s, 1H) 8.98 (dd, J=7.33, 1.77 Hz, 1H) 8.70 (dd, J=6.82, 1.77 Hz, 1H) 8.28 (s, 1H) 8.11 (t, J=7.71 Hz, 2H) 7.70 (dd, J=8.59, 7.33 Hz, 1H) 7.56-7.62 (m, 1H) 6.92 (t, J=7.20 Hz, 1H) 3.66-3.88 (m, 1H) 3.26 (m, 2H) 3.16 (m, 1H) 2.94 (br.s., 3H) 2.86-2.92 (m, 1H) 2.83 (d, J=4.04 Hz, 1H) 2.46-2.60 (m, 2H) 2.20-2.36 (m, 2H) 2.05-2.20 (m, 2H). MS [M+1]=401.

Example 12

N-[3-(dimethylamino)propyl]-N-methyl-12-oxo-12H-benzo[g]pyrido[2,1-b]quinazoline-4-carboxamide (compound 12)

This compound was synthesized from 3a (50 mg, 0.17 mmol) and N,N,N'-trimethyl-1,3-propanediamine (25.3 µL, 0.17 mmol) according to Method A to give N-[3-(dimethylamino)propyl]-N-methyl-12-oxo-12H-benzo[g]pyrido[2,1-b]quinazoline-4-carboxamide hydrochloride (27.7 mg, 0.071 mmol, 41.4% yield) as a yellow solid. $^1$H NMR (400 MHz, DMSO-d$_6$) δ ppm 9.12 (s, 1H) 8.77 (d, J=7.33 Hz, 1H) 8.32 (d, J=6.32 Hz, 2H) 8.10-8.21 (m, 1H) 7.54-7.75 (m, 3H) 6.90-7.01 (m, 1H) 3.41 (m, 2H) 3.10 (m, 3H) 2.87-2.93 (m, 8H) 2.13 (m, 2H). MS [M+1]=389.

Example 13

N-(1-methyl-4-piperidyl)-12-oxo-12H-benzo[g]pyrido[2,1-b]quinazoline-4-carboxamide (compound 13)

This compound was synthesized from 3a (50 mg, 0.17 mmol) and 4-amino-1-methylpiperidine (21.6 µL, 0.17 mmol) according to Method A to give N-(1-methyl-4-piperidyl)-12-oxo-12H-benzo[g]pyrido[2,1-b]quinazoline-4-carboxamide (32.4 mg, 0.084 mmol, 48.7% yield) as an orange solid. $^1$H NMR (400 MHz, CDCl$_3$) δ ppm 11.55 (d, J=8.34 Hz, 2H) 9.12 (s, 1H) 8.97 (dd, J=7.33, 1.77 Hz, 1H) 8.75 (dd, J=6.82, 1.77 Hz, 1H) 8.22 (s, 1H) 8.13 (d, J=8.84 Hz, 1H) 8.03 (d, J=8.59 Hz, 1H) 7.68-7.72 (m, 1H) 7.56-7.61 (m, 1H) 6.92 (t, J=7.07 Hz, 1H) 4.19 (br. s., 1H) 2.96 (br. s., 2H) 2.43 (s, 3H) 2.33 (br. s., 2H) 2.21 (d, J=9.60 Hz, 2H) 1.85-1.95 (m, 2H). MS [M+1]=387.

Example 14

N-(azetidin-3-yl)-12-oxo-12H-benzo[g]pyrido[2,1-b]quinazoline-4-carboxamide (compound 14)

A solution of compound 15 (76 mg, 0.17 mmol) in chloroform (1 mL) was treated with trifluoroacetic acid (1.5 mL, 19.6 mmol) at room temperature for 24 h (for convenience). The solvents were removed in vacuo to give N-(azetidin-3-yl)-12-oxo-12H-benzo[g]pyrido[2,1-b]quinazoline-4-carboxamide trifluoroacetate (76.1 mg, 0.17 mmol, 99% yield) as a yellow solid. $^1$H NMR (400 MHz, CDCl$_3$) δ ppm 9.14-9.20 (m, 1H) 9.10 (d, J=5.81 Hz, 1H) 8.67-8.74 (m, 1H) 8.46 (s, 1H) 8.20-8.27 (m, 1H) 8.12 (s, 1H) 7.92 (s, 1H) 7.75 (d, J=7.83 Hz, 1H) 7.65 (d, J=6.82 Hz, 1H) 7.11 (t, J=7.20 Hz, 1H) 4.67 (dd, J=7.07, 4.55 Hz, 1H) 4.53 (d, J=7.33 Hz, 2H) 2.83 (br.s., 3H). MS [M+1]=345.

Example 15

Tert-butyl 3-[(12-oxo-12H-benzo[g]pyrido[2,1-b]quinazoline-4-carbonyl)amino]azetidine-1-carboxylate (compound 15)

This compound was synthesized from 3a (50 mg, 0.17 mmol) and 1-Boc-3-(amino)azetidine (29.7 mg, 0.17 mmol) according to Method A to give tert-butyl 3-[(12-oxo-12H-benzo[g]pyrido[2,1-b]quinazoline-4-carbonyl)amino]azetidine-1-carboxylate (76 mg, 0.17 mmol, 99% yield) as a yellow-orange solid. $^1$H NMR (400 MHz, CDCl$_3$) δ ppm 11.98 (br. s., 1H) 9.15 (s, 1H) 9.00 (dd, J=7.33, 1.77 Hz, 1H) 8.73 (dd, J=7.07, 1.77 Hz, 1H) 8.25 (s, 1H) 8.13 (dd, J=17.56, 7.71 Hz, 2H) 7.70-7.76 (m, 1H) 7.58-7.64 (m, 1H) 6.91-6.95 (m, 1H) 4.90 (d, J=6.32 Hz, 1H) 4.46-4.53 (m, 2H) 4.11 (br. s., 2H) 1.52 (s, 9H). MS [M+1]=445.

Example 16

4-(4-isopropylpiperazine-1-carbonyl)-12H-benzo[g]pyrido[2,1-b]quinazoline-12-one (compound 16)

This compound was synthesized from 3a (50 mg, 0.17 mmol) and 1-isopropylpiperazine (26.4 µL, 0.17 mmol) according to Method A to give 4-(4-isopropylpiperazine-1-carbonyl)-12H-benzo[g]pyrido[2,1-b]quinazoline-12-one (40.9 mg, 0.102 mmol, 59.4% yield) as a yellow-orange solid. $^1$H NMR (400 MHz, CDCl$_3$) δ ppm 9.11-9.14 (m, 1H) 8.79-8.82 (m, 1H) 8.30 (s, 1H) 8.10-8.15 (m, 1H) 7.99-8.03 (m, 1H) 7.62-7.68 (m, 1H) 7.53-7.59 (m, 1H) 7.45 (dd, J=6.57, 1.52 Hz, 1H) 6.73-6.79 (m, 1H) 4.10 (m, 2H) 3.87 (m, 2H) 3.48 (m, 1H) 3.36 (m, 1H) 2.74-2.92 (m, 1H) 2.68 (m, 1H) 2.40 (m, 1H) 1.10 (d, J=6.57 Hz, 6H). MS [M+1]=401.

Example 17

N-methyl-N-(1-methylpyrrolidin-3-yl)-12-oxo-12H-benzo[g]pyrido[2,1-b]quinazoline-4-carboxamide (compound 17)

This compound was synthesized from 3a (50 mg, 0.17 mmol) and N,N'-dimethyl-3-aminopyrrolidine (19.7 mg, 0.17 mmol) according to Method A to give N-methyl-N-(1-methylpyrrolidin-3-yl)-12-oxo-12H-benzo[g]pyrido[2,1-b]quinazoline-4-carboxamide trifluoroacetate (6 mg, 0.016 mmol, 9.0% yield) as a yellow-orange solid. $^1$H NMR (400 MHz, MeOD) δ ppm 9.11 (s, 1H) 8.83-8.92 (m, 1H) 8.24-8.33 (m, 1H) 8.19 (d, J=8.08 Hz, 1H) 8.07 (d, J=8.34 Hz, 1H) 7.92 (s, 1H) 7.55-7.74 (m, 3H) 6.95 (q, J=7.33 Hz, 1H) 4.60 (d, J=9.35 Hz, 1H) 4.25 (d, J=11.87 Hz, 1H) 4.02-4.14 (m, 1H) 3.47-3.62 (m, 1H) 3.17-3.28 (m, 4H) 3.07 (m, 3H) 2.67-2.85 (m, 2H). MS [M+1]=387.

Example 18

4-[(3S)-3-(dimethylamino)pyrrolidine-1-carbonyl]-12H-benzo[g]pyrido[2,1-b]quinazoline-12-one (compound 18)

This compound was synthesized from 3a (50 mg, 0.17 mmol) and (3S)-(–)-3-(dimethylamino)pyrrolidine (19.7 mg, 0.17 mmol) according to Method A to give 4-[(3S)-3-(dimethylamino)pyrrolidine-1-carbonyl]-12H-benzo[g]pyrido[2,1-b]quinazoline-12-one hydrochloride (34.1 mg, 0.088 mmol, 51.2% yield) as a yellow-orange solid. $^1$H NMR (400 MHz, CDCl$_3$) δ ppm 1.96 (br. s., 2H) 9.12 (s, 1H) 8.82 (td, J=6.63, 1.64 Hz, 1H) 8.31-8.35 (m, 1H) 8.12 (d, J=8.59 Hz, 1H) 8.03 (d, J=8.08 Hz, 1H) 7.62-7.68 (m, 1H) 7.53-7.58 (m, 1H) 6.74-6.80 (m, 1H) 3.47 (m, 2H) 2.91 (m, 2H) 2.43-2.49 (m, 1H) 2.39 (s, 3H) 2.24-2.33 (m, 1H) 2.20 (s, 3H) 2.11 (m, 1H). MS [M+1]=387.

Example 19

4-[3-(diethylamino)pyrrolidine-1-carbonyl]-12H-benzo[g]pyrido[2,1-b]quinazoline-12-one (compound 19)

This compound was synthesized from 3a (50 mg, 0.17 mmol) and 3-(diethylamino)pyrrolidine (24.5 mg, 0.17 mmol) according to Method A to give 4-[3-(diethylamino)pyrrolidine-1-carbonyl]-12H-benzo[g]pyrido[2,1-b]quinazoline-12-one (54.7 mg, 0.13 mmol, 76.6% yield) as a yellow-orange solid. $^1$H NMR (400 MHz, CDCl$_3$) δ ppm 9.12 (s, 1H) 8.82 (dd, J=7.58, 1.52 Hz, 1H) 8.28-8.37 (m, 2H) 8.12 (d, J=8.59 Hz, 1H) 7.65-7.74 (m, 2H) 7.57-7.63 (m, 1H) 6.97-7.02 (m, 1H) 4.10 (m, 1H) 3.97 (m, 1H) 3.81-3.93 (m, 1H) 3.63 (m 1H) 3.38 (d, J=7.33 Hz, 1H) 3.14 (m, 1H) 2.87 (m, 1H) 2.33 (br. s., 1H) 2.26 (br. s., 1H) 1.33-1.38 (m, 1H) 1.26-1.33 (m, 1H) 1.14 (t, J=7.07 Hz, 3H) 1.01 (t, J=7.07 Hz, 3H). MS [M+1]=415.

Example 20

N-[2-(diethylamino)ethyl]-12-oxo-12H-benzo[g]pyrido[2,1-b]quinazoline-4-carboxamide (compound 20)

This compound was synthesized from 3a (50 mg, 0.17 mmol) and N',N'-diethylethane-1,2-diamine (24.3 μL, 0.17 mmol) according to Method A to give N-[2-(diethylamino)ethyl]-12-oxo-12H-benzo[g]pyrido[2,1-b]quinazoline-4-carboxamide (18.2 mg, 0.047 mmol, 27% yield) as a yellow-orange solid. $^1$H NMR (400 MHz, CDCl$_3$) δ ppm 11.56-11.65 (m, 1H) 9.12 (s, 1H) 8.94-8.99 (m, 1H) 8.75 (d, J=7.07 Hz, 1H) 8.41 (s, 1H) 8.14 (d, J=8.08 Hz, 1H) 8.01 (d, J=7.83 Hz, 1H) 7.68 (m, J=7.58 Hz, 1H) 7.51-7.62 (m, 1H) 6.91 (t, J=7.07 Hz, 1H) 3.77 (br. s., 2H) 2.83 (m, 6H) 1.21 (t, J=7.20 Hz, 6H). MS [M+1]=389.

Example 21

N-[2-(diisopropylamino)ethyl]-12-oxo-12H-benzo[g]pyrido[2,1-b]quinazoline-4-carboxamide (compound 21)

This compound was synthesized from 3a (50 mg, 0.17 mmol) and N,N-diisopropylethylenediamine (29.9 μL, 0.17 mmol) according to Method A to give N-[2-(diisopropylamino)ethyl]-12-oxo-12H-benzo[g]pyrido[2,1-b]quinazoline-4-carboxamide (33 mg, 0.079 mmol, 46% yield) as an orange solid. $^1$H NMR (400 MHz, DMSO-d$_6$) δ ppm 11.07 (br. s., 1H) 9.11 (s, 1H) 8.92 (d, J=7.33 Hz, 1H) 8.58 (d, J=6.32 Hz, 1H) 8.42 (s, 1H) 8.31 (d, J=7.83 Hz, 1H) 8.09 (d, J=7.83 Hz, 1H) 7.73 (t, J=7.07 Hz, 1H) 7.57-7.66 (m, 1H) 7.05 (t, J=7.33 Hz, 1H) 3.50 (d, J=5.56 Hz, 2H) 3.13-3.23 (m, 2H) 2.66-2.75 (m, 2H) 1.07 (d, J=6.57 Hz, 12H). $^1$H NMR (400 MHz, CDCl$_3$) δ ppm 11.33 (br. s., 1H) 9.12 (s, 1H) 8.96 (d, J=6.06 Hz, 1H) 8.76 (d, J=6.57 Hz, 1H) 8.36 (s, 1H) 8.13 (d, J=8.08 Hz, 1H) 8.01 (d, J=9.09 Hz, 1H) 7.63-7.72 (m, 1H) 7.52-7.61 (m, 1H) 6.90 (t, J=7.07 Hz, 1H) 3.66 (d, J=5.56 Hz, 2H) 3.22 (d, J=6.57 Hz, 2H) 2.81 (br. s., 2H) 1.14 (d, J=6.32 Hz, 12H). MS [M+1]=417.

Example 22

12-oxo-N-(2-pyrrolidin-1-ylethyl)-12H-benzo[g]pyrido[2,1-b]quinazoline-4-carboxamide (compound 22)

This compound was synthesized from 3a (50 mg, 0.17 mmol) and 2-pyrrolidin-1-ylethanamine (21.8 μL, 0.17 mmol) according to Method A to give 12-oxo-N-(2-pyrrolidin-1-ylethyl)-12H-benzo[g]pyrido[2,1-b]quinazoline-4-carboxamide (32.4 mg, 0.084 mmol, 48.7% yield) as a yellow-orange solid. $^1$H NMR (400 MHz, CDCl$_3$) δ ppm 11.65 (br. s., 1H) 9.11 (s, 1H) 8.96 (dd, J=7.20, 1.64 Hz, 1H) 8.71-8.77 (m, 1H) 8.37 (s, 1H) 8.13 (d, J=8.34 Hz, 1H) 8.02 (d, J=7.83 Hz, 1H) 7.64-7.72 (m, 1H) 7.54-7.63 (m, 1H) 6.87-6.94 (m, 1H) 3.79-3.88 (m, 2H) 2.96-3.03 (m, 2H) 2.89 (m, 2H) 2.78 (m, 2H) 2.00 (m, 4H). MS [M+1]=387.

Example 23

12-oxo-N-[2-(1-piperidyl)ethyl]-12H-benzo[g]pyrido[2,1-b]quinazoline-4-carboxamide (compound 23)

This compound was synthesized from 3a (50 mg, 0.17 mmol) and 1-(2-aminoethyl)piperidine (24.6 μL, 0.17 mmol) according to Method A to give 12-oxo-N-[2-(1-piperidyl)ethyl]-12H-benzo[g]pyrido[2,1-b]quinazoline-4-carboxamide (25 mg, 0.062 mmol, 36.2% yield) as an orange solid. $^1$H NMR (400 MHz, CDCl3) δ ppm 11.48 (br. s., 1H) 9.12 (s, 1H) 8.96 (dd, J=7.33, 1.77 Hz, 1H) 8.74 (dd, J=6.95, 1.64 Hz, 1H) 8.44 (s, 1H) 8.13 (d, J=8.34 Hz, 1H) 8.00 (d, J=8.34 Hz, 1H) 7.68 (dd, J=8.08, 7.07 Hz, 1H) 7.53-7.61 (m, 1H) 6.90 (t, J=7.07 Hz, 1H) 3.75 (q, J=5.81 Hz, 2H) 2.73 (t, J=6.19 Hz, 2H) 2.61 (br. s., 4H) 1.78 (dt, J=11.24, 5.75 Hz, 4H) 1.54-1.59 (m, 2H). MS [M+1]=401.

Example 24

N-(2-morpholinoethyl)-12-oxo-12H-benzo[g]pyrido[2,1-b]quinazoline-4-carboxamide (compound 24)

This compound was synthesized from 3a (50 mg, 0.17 mmol) and N-(2-aminoethyl)morpholine (22.6 μL, 0.17 mmol) according to Method A to give N-(2-morpholinoethyl)-12-oxo-12H-benzo[g]pyrido[2,1-b]quinazoline-4-carboxamide (28.7 mg, 0.071 mmol, 41.4% yield) as an orange solid. $^1$H NMR (400 MHz, DMSO-d6) δ ppm 11.50 (br. s., 1H) 9.12 (s, 1H) 8.96 (dd, J=7.33, 1.77 Hz, 1H) 8.75 (dd, J=6.82, 1.77 Hz, 1H) 8.38 (s, 1H) 8.13 (d, J=8.59 Hz, 1H) 8.00 (d, J=8.34 Hz, 1H) 7.64-7.73 (m, 1H) 7.54-7.62 (m, 1H) 6.90 (t, J=7.07 Hz, 1H) 3.88-3.97 (m, 4H) 3.77 (q, J=5.89 Hz, 2H) 2.78 (t, J=6.19 Hz, 2H) 2.68 (br. s., 4H). MS [M+1]=403.

Example 25

N-[2-(4-methylpiperazin-1-yl)ethyl]-12-oxo-12H-benzo[g]pyrido[2,1-b]quinazoline-4-carboxamide (compound 25)

This compound was synthesized from 3a (50 mg, 0.17 mmol) and 2-(4-methylpiperazin-1-yl)ethanamine (27.6 µL, 0.17 mmol) according to Method A to give N-[2-(4-methylpiperazin-1-yl)ethyl]-12-oxo-12H-benzo[g]pyrido[2,1-b]quinazoline-4-carboxamide (11.7 mg, 0.028 mmol, 16.3% yield) as a yellow-orange solid. $^1$H NMR (400 MHz, CDCl$_3$) δ ppm 11.46 (br. s., 1H) 9.14 (s, 1H) 8.98 (dd, J=7.33, 1.77 Hz, 1H) 8.76 (dd, J=6.82, 1.77 Hz, 1H) 8.43 (s, 1H) 8.16 (d, J=8.59 Hz, 1H) 8.08 (d, J=8.34 Hz, 1H) 7.65-7.73 (m, 1H) 7.60 (dd, J=6.82, 1.26 Hz, 1H) 6.92 (t, J=7.07 Hz, 1H) 3.74-3.83 (m, 2H) 2.60-2.88 (m, 10H) 2.38 (s, 3H). MS [M+1]=416.

Example 26

N-[2-[2-methoxyethyl(methyl)amino]ethyl]-12-oxo-12H-benzo[g]pyrido[2,1-b]quinazoline-4-carboxamide (compound 26)

This compound was synthesized from 3a (50 mg, 0.17 mmol) and N'-(2-methoxyethyl)-N'-methyl-ethane-1,2-diamine (27.3 mg, 0.21 mmol) according to Method A to give N-[2-[2-methoxyethyl(methyl)amino]ethyl]-12-oxo-12H-benzo[g]pyrido[2,1-b]quinazoline-4-carboxamide trifluoroacetate (15 mg, 0.037 mmol, 21.5% yield) as an orange gum. $^1$H NMR (400 MHz, CDCl$_3$) δ ppm 11.79 (br. s., 1H) 9.10 (s, 2H) 9.00 (dd, J=7.33, 1.52 Hz, 1H) 8.68-8.73 (m, 1H) 8.43 (s, 1H) 8.10 (dd, J=13.64, 8.34 Hz, 3H) 7.70 (t, J=7.58 Hz, 2H) 7.56-7.62 (m, 2H) 6.94 (t, J=7.20 Hz, 1H) 4.07 (br. s., 2H) 3.80 (t, J=4.55 Hz, 2H) 3.68 (br. s., 1H) 3.55 (br. s., 2H) 3.36-3.41 (m, 4H) 3.07 (s, 3H). $^{19}$F NMR (376 MHz, CDCl$_3$) δ ppm–170.87 (br. s., 3F). MS [M+1]=405.

Example 27

N-[2-(dimethylamino)-1-methyl-ethyl]-12-oxo-12H-benzo[g]pyrido[2,1-b]quinazoline-4-carboxamide (compound 27)

This compound was synthesized from 3a (50 mg, 0.17 mmol) and N1,N1-dimethylpropane-1,2-diamine (22.2 µL, 0.17 mmol) according to Method A to give N-[2-(dimethylamino)-1-methyl-ethyl]-12-oxo-12H-benzo[g]pyrido[2,1-b]quinazoline-4-carboxamide hydrochloride (38.7 mg, 0.103 mmol, 60% yield) as a yellow-orange solid. $^1$H NMR (400 MHz, CDCl$_3$) δ ppm 9.12 (s, 1H) 8.82 (td, J=6.63, 1.64 Hz, 1H) 8.31-8.35 (m, 1H) 8.12 (d, J=8.59 Hz, 1H) 8.03 (d, J=8.08 Hz, 1H) 7.62-7.68 (m, 1H) 7.53-7.58 (m, 1H) 6.74-6.80 (m, 1H) 3.47 (br. s., 1H) 2.91 (br. s., 1H) 2.43-2.49 (m, 1H) 2.39 (s, 3H) 2.20 (s, 3H) 1.96 (br. s., 3H). MS [M+1]=375.

Example 28

N-[2-(dimethylamino)propyl]-12-oxo-12H-benzo[g]pyrido[2,1-b]quinazoline-4-carboxamide (compound 28)

This compound was synthesized from 3a (50 mg, 0.17 mmol) and 2-(dimethylamino)propan-1-amine (21.1 mg, 0.21 mmol) according to Method A to give N-[2-(dimethylamino)propyl]-12-oxo-12H-benzo[g]pyrido[2,1-b]quinazoline-4-carboxamide (52 mg, 0.139 mmol, 80.6% yield) as a yellow solid. $^1$H NMR (400 MHz, CDCl$_3$) δ ppm 11.70 (br. s., 1H) 9.09 (s, 1H) 8.94 (dd, J=7.33, 1.77 Hz, 1H) 8.73 (dd, J=6.82, 1.77 Hz, 1H) 8.27 (s, 1H) 8.12 (d, J=8.59 Hz, 1H) 7.99 (d, J=8.59 Hz, 1H) 7.66 (dd, J=7.96, 6.95 Hz, 1H) 7.53-7.58 (m, 1H) 6.89 (t, J=7.07 Hz, 1H) 3.77 (dt, J=14.02, 5.62 Hz, 1H) 3.40-3.48 (m, 1H) 2.95-3.05 (m, 1H) 2.51 (s, 6H) 1.15 (d, J=6.32 Hz, 3H). MS [M+1]=375.

Example 29

N-(1-methylazetidin-3-yl)-12-oxo-12H-benzo[g]pyrido[2,1-b]quinazoline-4-carboxamide (compound 29)

This compound was synthesized from 3a (50 mg, 0.17 mmol) and 1-methylazetidin-3-amine dihydrochloride (28.4 uL, 0.26 mmol) according to Method A to give crude product, which was purified by automated normal-phase chromatography (0-20% MeOH/DCM, 4 g silica gel cartridge) to give N-(1-methylazetidin-3-yl)-12-oxo-12H-benzo[g]pyrido[2,1-b]quinazoline-4-carboxamide (32.8 mg, 0.092 mmol, 53.1% yield) as a red-orange glass. 1H NMR (400 MHz, DMSO-d6) δ ppm 11.45 (d, J=6.57 Hz, 1H) 9.11 (s, 1H) 8.93 (dd, J=7.33, 1.77 Hz, 1H) 8.50 (dd, J=6.82, 1.77 Hz, 1H) 8.42 (s, 1H) 8.31 (d, J=8.59 Hz, 1H) 8.20 (d, J=8.59 Hz, 1H) 7.71-7.76 (m, 1H) 7.59-7.64 (m, 1H) 7.05 (t, J=7.07 Hz, 1H) 4.54-4.63 (m, 1H) 3.84 (t, J=7.83 Hz, 2H) 3.35-3.38 (m, 2H) 2.47 (s, 3H) MS [M+1]=359.

Example 30

N-(2-amino-2-methyl-propyl)-12-oxo-12H-benzo[g]pyrido[2,1-b]quinazoline-4-carboxamide (compound 30)

This compound was synthesized from 3a (100 mg, 0.34 mmol) and 2-methylpropane-1,2-diamine (106 uL, 1.03 mmol) according to Method A to give N-(2-amino-2-methylpropyl)-12-oxo-12H-benzo[g]pyrido[2,1-b]quinazoline-4-carboxamide (110 mg, 0.31 mmol, 88.6% yield) as an orange solid. 1H NMR (400 MHz, DMSO-d6) δ ppm 11.38 (t, J=5.31 Hz, 1H) 9.12 (s, 1H) 8.92 (dd, J=7.33, 1.77 Hz, 1H) 8.54 (dd, J=6.95, 1.64 Hz, 1H) 8.38 (s, 1H) 8.31 (d, J=8.34 Hz, 1H) 8.13 (d, J=8.59 Hz, 1H) 7.73 (dd, J=8.34, 6.82 Hz, 1H) 7.58-7.63 (m, 1H) 7.06 (t, J=7.07 Hz, 1H) 3.34-3.40 (m, 2H) 2.69 (s, 2H) 1.21 (s, 6H) MS [M+1]=361.

Example 31

Method B: Bis-methylation of primary amine N-[2-(dimethylamino)-2-methyl-propyl]-12-oxo-12H-benzo[g]pyrido[2,1-b]quinazoline-4-carboxamide (compound 31)

To a solution of compound 30 (77 mg, 0.21 mmol) in MeCN (1.5 mL) and trimethyl orthoformate (0.50 mL) was added formaldehyde (128 uL, 2.14 mmol), sodium cyanoborohydride (85 mg, 2.14 mmol) and one drop of glacial acetic acid. The contents were stirred at room temperature for 4 h, then treated with 1M NaOH, taken up in EtOAc, washed with 10% Na2CO3 (3×), brine, dried over MgSO4, filtered and the solvent removed in vacuo to give an orange residue. This material was purified by automated normal-phase chromatography (0-20% MeOH/DCM, 4 g silica gel cartridge) to give N-[2-(dimethylamino)-2-methyl-propyl]-12-oxo-12H-benzo[g]pyrido[2,1-b]quinazoline-4-carboxamide (45 mg, 0.12 mmol, 54% yield) as an orange solid. 1H NMR (400 MHz, CDCl3) δ ppm 11.87 (br. s., 1H) 9.11 (s, 1H) 8.95 (dd, J=7.33, 1.77 Hz, 1H) 8.73 (dd, J=7.07, 1.77 Hz, 1H) 8.29 (s, 1H) 8.13 (d, J=8.34 Hz, 1H) 8.00 (d, J=8.34 Hz, 1H) 7.67 (ddd, J=8.27, 6.88, 1.26 Hz, 1H) 7.56 (ddd, J=8.21, 6.82, 1.14 Hz, 1H) 6.90 (t, J=7.07 Hz, 1H) 3.63 (d, J=4.80 Hz, 2H) 2.56 (s, 6H) 1.28 (s, 6H) MS [M+1]=389.

Example 32

N-(2-aminopropyl)-12-oxo-12H-benzo[g]pyrido[2,1-b]quinazoline-4-carboxamide (compound 32)

This compound was synthesized from 3a (100 mg, 0.17 mmol) and 1,2-diaminopropane (88 uL, 1.03 mmol) according to Method A to give crude product, which was purified by automated normal-phase chromatography (0-20% MeOH/DCM, 4 g silica gel cartridge) to give N-(2-aminopropyl)-12-oxo-12H-benzo[g]pyrido[2,1-b]quinazoline-4-carboxamide (23.9 mg, 0.069 mmol, 20% yield) as an orange solid. 1H NMR (400 MHz, DMSO-d6) δ ppm 11.27 (br. s., 1H) 9.11 (s, 1H) 8.92 (dd, J=7.20, 1.64 Hz, 1H) 8.52 (dd, J=6.82, 1.77 Hz, 1H) 8.43 (s, 1H) 8.31 (d, J=8.59 Hz, 1H) 8.14 (d, J=8.59 Hz, 1H) 7.73 (t, J=7.71 Hz, 1H) 7.58-7.63 (m, 1H) 7.06 (t, J=7.07 Hz, 1H) 3.42-3.51 (m, 1H) 3.35-3.39 (m, 1H) 3.20 (dd, J=12.51, 5.94 Hz, 1H) 1.19 (d, J=6.57 Hz, 3H) MS [M+1]=347.

Example 33

N-[(2R)-2-aminopropyl]-12-oxo-12H-benzo[g]pyrido[2,1-b]quinazoline-4-carboxamide (compound 33)

This compound was synthesized from 3a (100 mg, 0.17 mmol) and (2R)-propane-1,2-diamine dihydrochloride (152 mg, 1.03 mmol) according to Method A to give crude product, which was purified by automated normal-phase chromatography (0-30% MeOH/DCM, 4 g silica gel cartridge) to give N-[(2R)-2-aminopropyl]-12-oxo-12H-benzo[g]pyrido[2,1-b]quinazoline-4-carboxamide (42.2 mg, 0.122 mmol, 35% yield) as a yellow-orange solid. 1H NMR (400 MHz, CDCl3) δ ppm 11.57 (br. s., 1H) 9.12 (s, 1H) 8.97 (dd, J=7.20, 1.64 Hz, 1H) 8.75 (dd, J=6.82, 1.52 Hz, 1H) 8.28 (s, 1H) 8.12 (d, J=8.08 Hz, 1H) 8.03 (d, J=8.59 Hz, 1H) 7.67 (dd, J=8.21, 6.95 Hz, 1H) 7.54-7.60 (m, 1H) 6.91 (t, J=7.07 Hz, 1H) 3.71 (dt, J=13.14, 5.31 Hz, 1H) 3.33-3.48 (m, 2H) 1.31 (d, J=6.32 Hz, 3H) MS [M+1]=347.

Example 34

N-[(2R)-2-(dimethylamino)propyl]-12-oxo-12H-benzo[g]pyrido[2,1-b]quinazoline-4-carboxamide (compound 34)

This compound was synthesized from compound 33 (35 mg, 0.10 mmol) according to Method B to give crude product, which was purified by automated normal-phase chromatography (0-20% MeOH/DCM, 4 g silica gel cartridge) to give N-[(2R)-2-aminopropyl]-12-oxo-12H-benzo[g]pyrido[2,1-b]quinazoline-4-carboxamide (22.3 mg, 0.060 mmol, 59% yield) as a yellow-orange solid. 1H NMR (400 MHz, CDCl3) δ ppm 11.73 (br. s., 1H) 9.11 (s, 1H) 8.95 (dd, J=7.33, 1.77 Hz, 1H) 8.73 (dd, J=7.07, 1.77 Hz, 1H) 8.29 (s, 1H) 8.12 (d, J=8.34 Hz, 1H) 8.01 (d, J=8.08 Hz, 1H) 7.67 (ddd, J=8.34, 6.82, 1.26 Hz, 1H) 7.56 (ddd, J=8.27, 6.88, 1.26 Hz, 1H) 6.89 (t, J=7.07 Hz, 1H) 3.74-3.81 (m, 1H) 3.47 (ddd, J=14.08, 8.78, 3.41 Hz, 1H) 3.00-3.08 (m, 1H) 2.53 (s, 6H) 1.17 (d, J=6.57 Hz, 3H) MS [M+1]=375.

Example 35

N-[(2S)-2-aminopropyl]-12-oxo-12H-benzo[g]pyrido[2,1-b]quinazoline-4-carboxamide (compound 35)

This compound was synthesized from 3a (100 mg, 0.17 mmol) and (2R)-propane-1,2-diamine dihydrochloride (152 mg, 1.03 mmol) according to Method A to give crude product, which was purified by automated normal-phase chromatography (0-30% MeOH/DCM, 4 g silica gel cartridge) to give N-[(2S)-2-aminopropyl]-12-oxo-12H-benzo[g]pyrido[2,1-b]quinazoline-4-carboxamide (33.1 mg, 0.096 mmol, 28% yield) as a yellow-orange solid. 1H NMR (400 MHz, CDCl3) δ ppm 11.57 (br. s., 1H) 9.12 (s, 1H) 8.97 (dd, J=7.33, 1.77 Hz, 1H) 8.75 (dd, J=6.82, 1.77 Hz, 1H) 8.28 (s, 1H) 8.13 (d, J=8.08 Hz, 1H) 8.03 (d, J=8.34 Hz, 1H) 7.67 (ddd, J=8.27, 6.88, 1.26 Hz, 1H) 7.54-7.59 (m, 1H) 6.91 (t, J=7.20 Hz, 1H) 3.71 (ddd, J=13.07, 5.87, 4.55 Hz, 1H) 3.33-3.51 (m, 2H) 1.31 (d, J=6.32 Hz, 3H) MS [M+1]=347.

Example 36

N-[(2S)-2-(dimethylamino)propyl]-12-oxo-12H-benzo[g]pyrido[2,1-b]quinazoline-4-carboxamide (compound 36)

This compound was synthesized from compound 35 (26.5 mg, 0.080 mmol) according to Method B to give crude product, which was purified by automated normal-phase chromatography (0-20% MeOH/DCM, 4 g silica gel cartridge) to give N-[(2S)-2-aminopropyl]-12-oxo-12H-benzo[g]pyrido[2,1-b]quinazoline-4-carboxamide (19 mg, 0.051 mmol, 66% yield) as a yellow-orange solid. 1H NMR (400 MHz, CDCl3) δ ppm 11.71 (br. s., 1H) 9.11 (s, 1H) 8.94 (dd, J=7.33, 1.77 Hz, 1H) 8.73 (dd, J=7.07, 1.77 Hz, 1H) 8.28 (s, 1H) 8.12 (d, J=8.08 Hz, 1H) 8.00 (d, J=8.08 Hz, 1H) 7.67 (ddd, J=8.27, 6.88, 1.26 Hz, 1H) 7.56 (ddd, J=8.21, 6.82, 1.14 Hz, 1H) 6.89 (t, J=7.07 Hz, 1H) 3.77 (ddd, J=14.02, 6.06, 5.18 Hz, 1H) 3.45 (ddd, J=13.96, 8.91, 3.41 Hz, 1H) 2.97-3.06 (m, 1H) 2.52 (s, 6H) 1.16 (d, J=6.57 Hz, 3H) MS [M+1]=375.

Example 37

12-oxo-N-[2-(4-pyridyl)ethyl]-12H-benzo[g]pyrido[2,1-b]quinazoline-4-carboxamide (compound 37)

This compound was synthesized from 3a (50 mg, 0.17 mmol) and 4-(2-aminoethyl)pyridine (20.8 μL, 0.17 mmol) according to Method A to give 12-oxo-N-[2-(4-pyridyl)ethyl]-12H-benzo[g]pyrido[2,1-b]quinazoline-4-carboxamide (43.5 mg, 0.11 mmol, 64% yield) as an orange solid. $^1$H NMR (400 MHz, CDCl$_3$) δ ppm 11.42 (br. s., 1H) 9.09 (s, 1H) 8.97 (dd, J=7.33, 1.77 Hz, 1H) 8.76 (dd, J=7.07, 1.77 Hz, 1H) 8.62-8.67 (m, 2H) 8.09 (dd, J=17.81, 8.46 Hz, 2H) 7.66-7.74 (m, 1H) 7.54-7.62 (m, 1H) 7.48 (s, 1H) 7.37 (d, J=6.06 Hz, 2H) 6.92 (t, J=7.07 Hz, 1H) 3.97-4.08 (m, 2H) 3.05-3.15 (m, 2H). MS [M+1]=395.

Example 38

2-(dimethylamino)ethyl 12-oxo-12H-benzo[g]pyrido[2,1-b]quinazoline-4-carboxylate This compound was synthesized from 3a (50 mg, 0.17 mmol) and 2-dimethylaminoethanol (41.6 µL, 0.41 mmol) according to Method A to give 2-(dimethylamino)ethyl 12-oxo-12H-benzo[g]pyrido[2,1-b]quinazoline-4-carboxylate (47 mg, 0.13 mmol, 47.2% yield) as an orange solid. $^1$H NMR (400 MHz, CDCl$_3$) δ ppm 9.10 (s, 1H) 8.87 (dd, J=7.45, 1.64 Hz, 1H) 8.36 (s, 1H) 8.11 (d, J=8.34 Hz, 1H) 8.02 (d, J=8.34 Hz, 1H) 7.78 (dd, J=6.69, 1.64 Hz, 1H) 7.64 (ddd, J=8.27, 6.76, 1.14 Hz, 1H) 7.52-7.57 (m, 1H) 6.72 (dd, J=7.33, 6.57 Hz, 1H) 4.58 (t, J=5.81 Hz, 2H) 2.80 (t, J=5.68 Hz, 2H) 2.38 (s, 6H). MS [M+1]=362.

As the data herein indicate, a broad variety of compounds of formula I were found effective at low concentrations. IC$_{50}$ values for exemplary compounds of formula I (see above for compound names and structures) are provided in Table 1 below.

TABLE 1

Compounds and their efficacies

| ID | RPA194 (IC$_{50}$ µM) | NCL (IC$_{50}$ µM) |
|---|---|---|
| Compound 1 | 22 | NT |
| Compound 2 | >100 | >100 |
| Compound 3 | 1 | 26 |
| Compound 4 | 16 | >100 |
| Compound 5 | 12 | >100 |
| Compound 6 | 13 | 2 |
| Compound 7 | 32 | >100 |
| Compound 8 | 5 | >100 |
| Compound 9 | 0.43 | 0.48 |
| Compound 10 | 0.66 | 1.53 |
| Compound 11 | 2.0 | 2.6 |
| Compound 12 | 33 | >100 |
| Compound 13 | 0.18 | 1.38 |
| Compound 14 | 0.21 | 0.18 |
| Compound 15 | 35 | >100 |
| Compound 16 | >100 | >100 |
| Compound 17 | 42 | >100 |
| Compound 18 | >100 | >100 |
| Compound 19 | 32 | 11 |
| Compound 20 | 0.14 | 0.19 |
| Compound 21 | 3.0 | 1.7 |
| Compound 22 | 0.09 | 0.08 |
| Compound 23 | 0.18 | 0.08 |
| Compound 24 | 1.3 | 0.60 |
| Compound 25 | 1.1 | 1.8 |
| Compound 26 | 0.73 | 0.70 |
| Compound 27 | 0.11 | 0.16 |
| Compound 28 | 0.04 | 0.04 |
| Compound 29 | 0.90 | 0.47 |
| Compound 30 | 0.27 | 0.20 |
| Compound 31 | 0.16 | 0.14 |
| Compound 32 | 0.10 | 0.10 |
| Compound 33 | 0.11 | 0.81 |
| Compound 34 | 0.26 | 0.05 |
| Compound 35 | 0.12 | 0.17 |
| Compound 36 | 0.04 | 0.04 |
| Compound 37 | 3.5 | >100 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I:

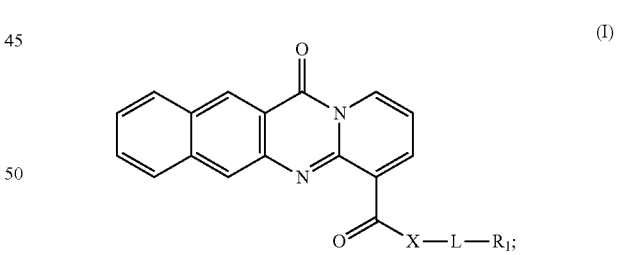

(I)

wherein X is NR$_2$;
wherein L is R$_3$ or a cycloamine

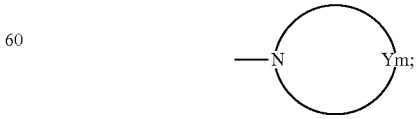

wherein R$_1$ is a straight-chained or branched C$_1$-C$_6$ alkyl or hydroxyalkyl, or R$_1$ is phenyl, benzyl, cycloalkyl, heterocyclyl, or indolyl, wherein each of alkyl, phenyl, or heterocyclyl moiety is unsubstituted or substituted with one or more substituents selected from the group consisting of halo, hydroxy, carboxy, phosphoryl, phosphoryl, phosphono $C_1$-$C_6$ alkyl, carboxy $C_1$-$C_6$ alkyl, dicarboxy $C_1$-$C_6$ alkyl, dicarboxy halo-$C_1$-$C_6$ alkyl, —$SO_2Me$, cyano, nitro, alkylthio, aryloxy, amino, alkylamino, dialkylamino, trialkylamino, arylalkylamino, guanidino, ureide, aminocarbonyl, a branched or straight-chain alkyl or dialkylaminoalkyl, thioalkyl, thioalkenyl, thioalkynyl, amido, and sulphonamido groups;

$R_2$ is H or a straight-chained $C_1$-$C_6$ alkyl group;

when L is $R_3$, $R_3$ is a straight-chained or branched $C_2$-$C_6$ alkyl group;

when L is

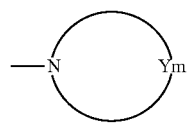

m=1-2 and each Y is independently selected from $(CH_2)_n Y^1_p$ wherein n=1-3, p=0-1 and the sum of n and p is at least 2, and each $Y^1$ is independently selected from $NR_4$, O, S, and P, wherein $R_4$ is a straight-chained or branched $C_2$-$C_6$ alkyl group; and provided that the compound is not:

BMH-21a1

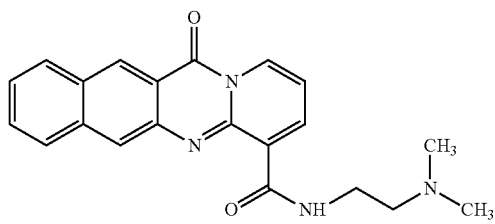

or a pharmaceutically acceptable salt, solvate, or stereoisomer thereof.

2. The compound of claim 1, wherein L is $R_3$ and $R_3$ is a straight-chained or branched $C_2$-$C_6$ alkyl group.

3. A compound of formula II, (II)

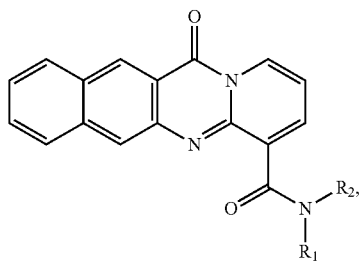

wherein $R_1$=H and $R_2$=$C_1$-$C_6$ alkyl, substituted with one or more $C_1$-$C_4$ alkyl, OH, $NH_2$, $NR_3R_4$, cyano, $SO_2R_3$, aryl, heteroaryl selected from the group consisting of imidazolyl, imidazolidinonyl, indolyl, oxazolyl, thiazolyl, and oxadiazolyl, cycloalkyl, or nitrogen-containing heterocycles;

wherein $R_3$ and $R_4$, are independently selected from the group consisting of H, $C_1$-$C_6$ alkyl, and $C_1$-$C_4$ alkoxy alkyl, having at least one chiral carbon, when $R_2$ is substituted with at least one $NR_3R_4$ group, and provided that the compound is not:

BMH-21a1

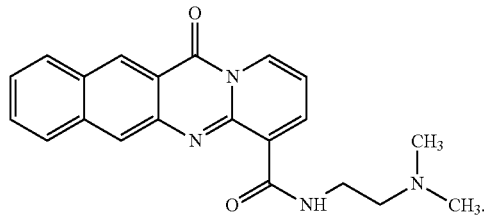

4. The compound of claim 3, wherein $R_2$ is substituted with at least one $NR_3R_4$ group.

5. A compound selected from the group consisting of:

compound 1

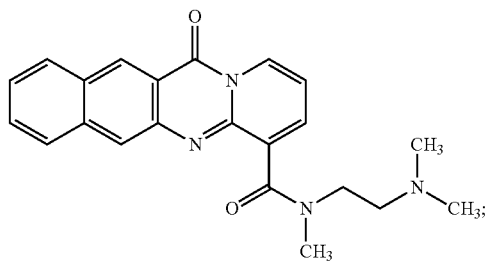

compound 3

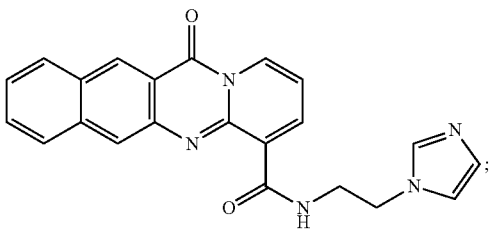

compound 4

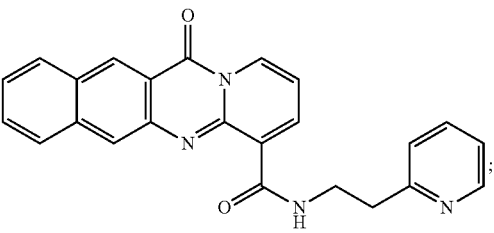

compound 5

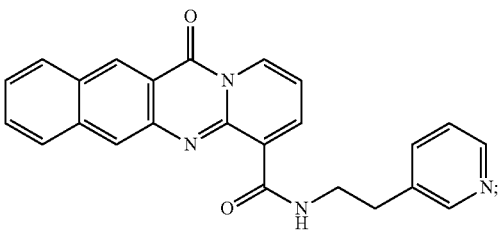

compound 6
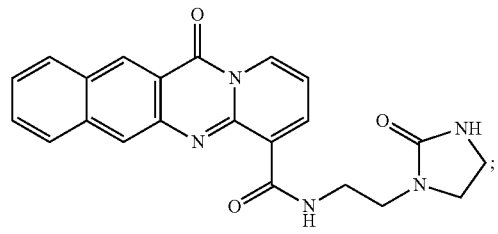
compound 7
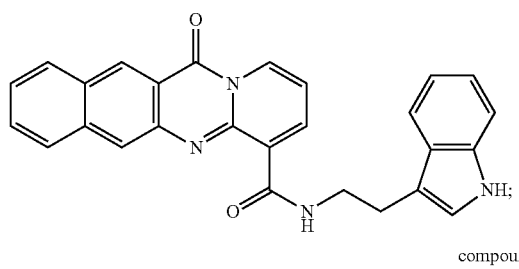
compound 8
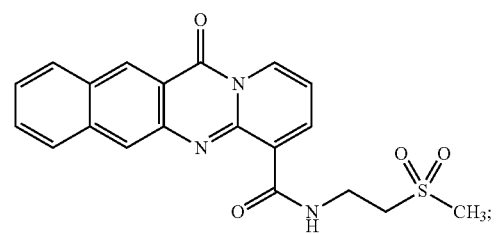
compound 9
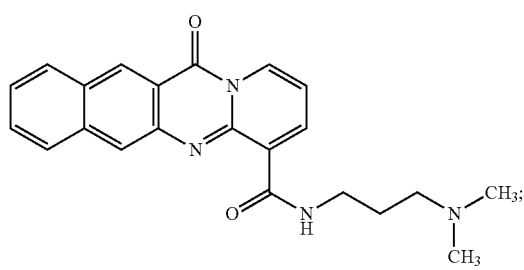
compound 10
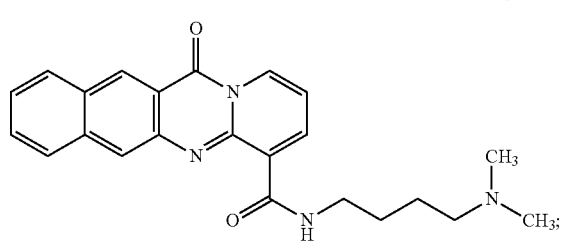
compound 11
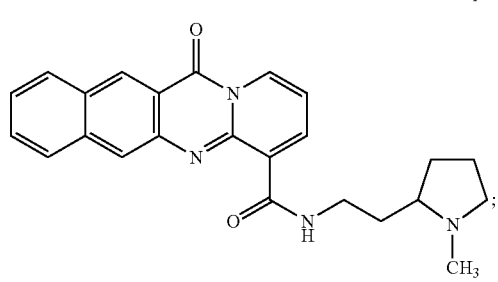
compound 12
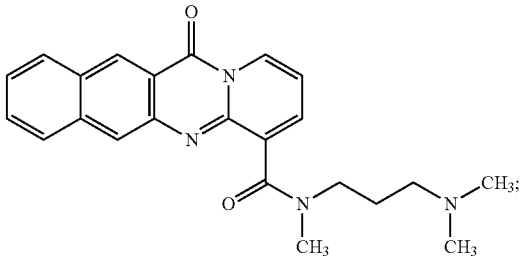
compound 13
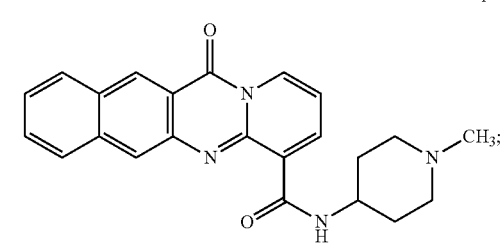
compound 14
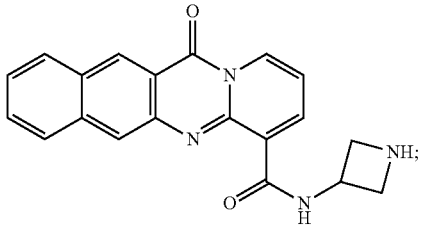
compound 15
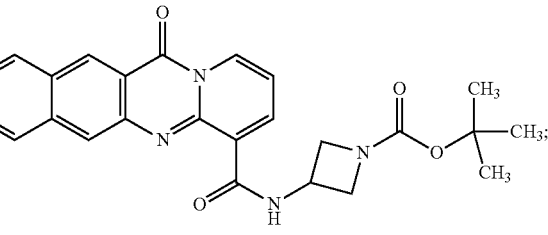
compound 17
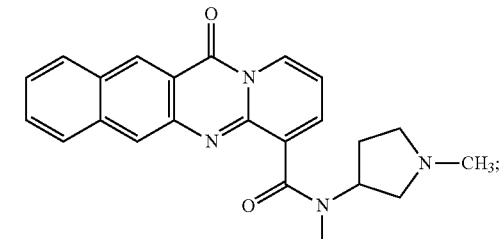
compound 19
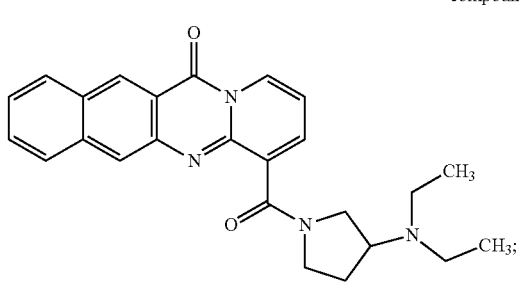

compound 22
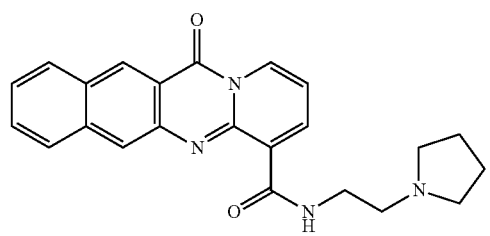
compound 23
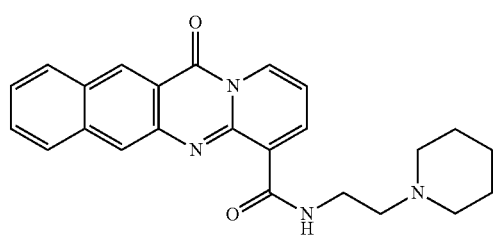
compound 24
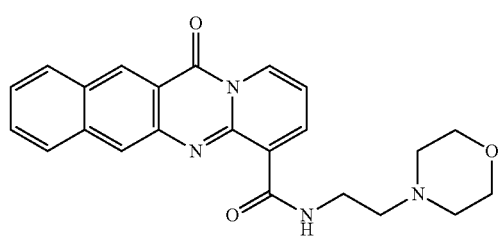
compound 25
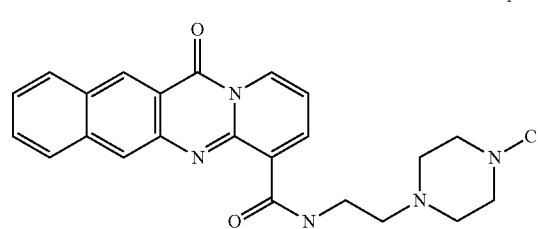
compound 27
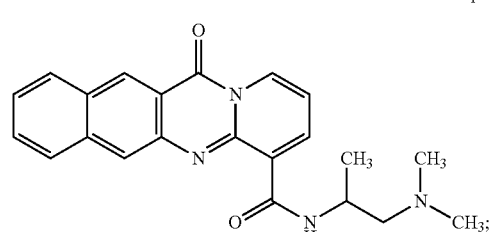
compound 28
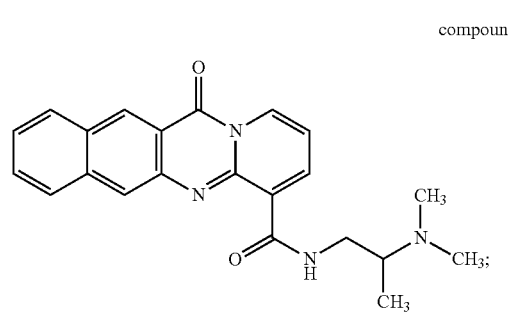
compound 29
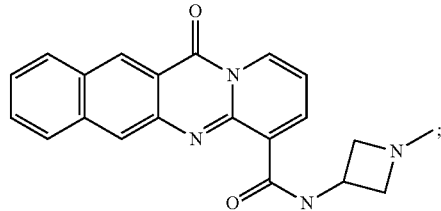
compound 30
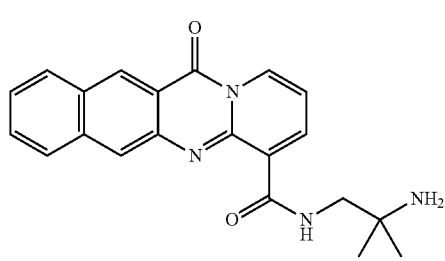
compound 31
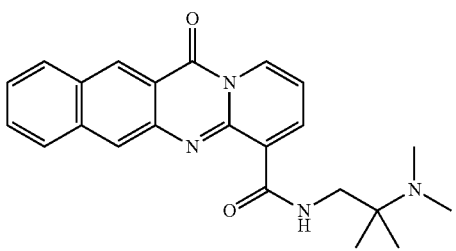
compound 32
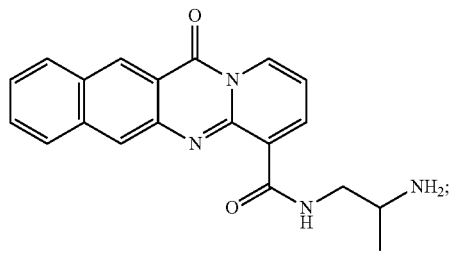
compound 33
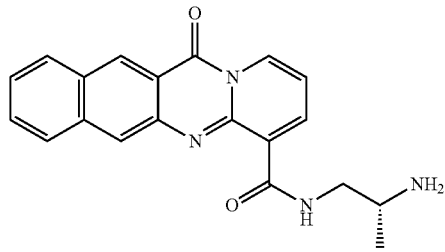

compound 35
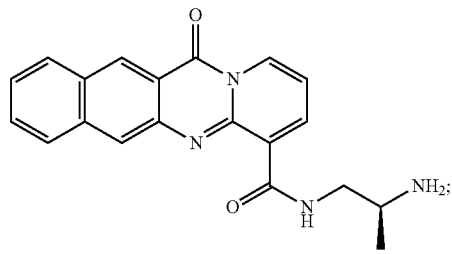
compound 36
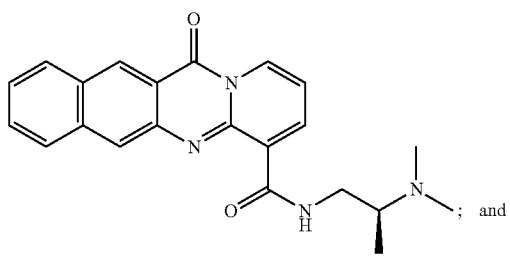
; and
compound 37
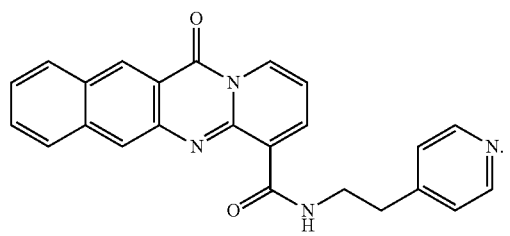
6. A pharmaceutical composition comprising a compound of claim 1, and a pharmaceutically acceptable carrier.
7. A pharmaceutical composition comprising a compound selected from the group consisting of
compound 1
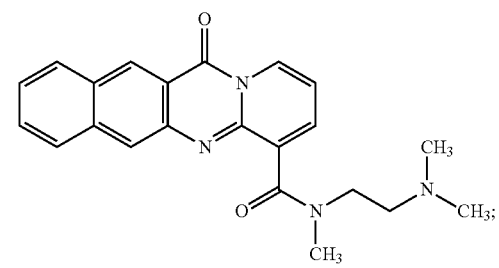
compound 3
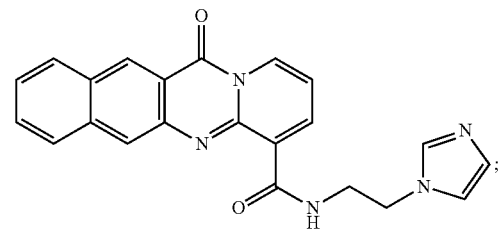
compound 4
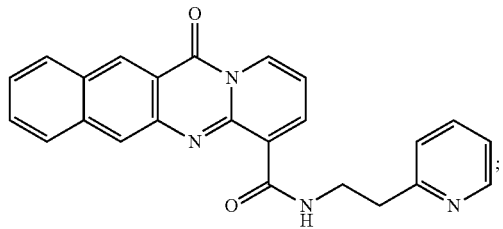
compound 5
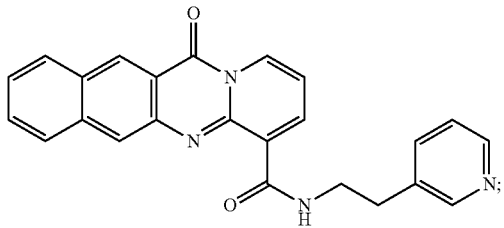
compound 6
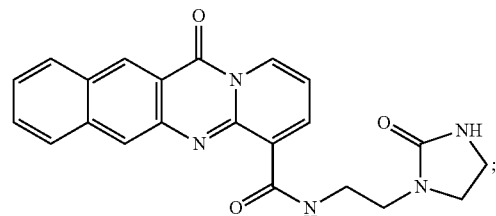
compound 7
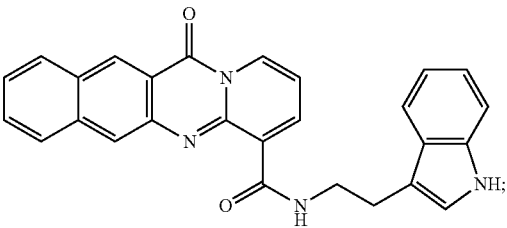
compound 8
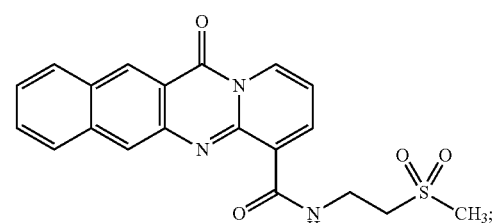
compound 9
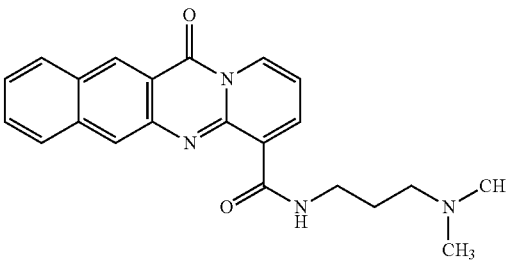

compound 10
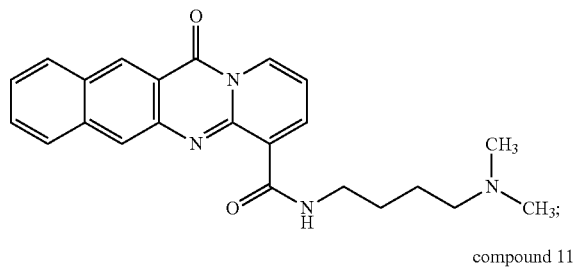
compound 11
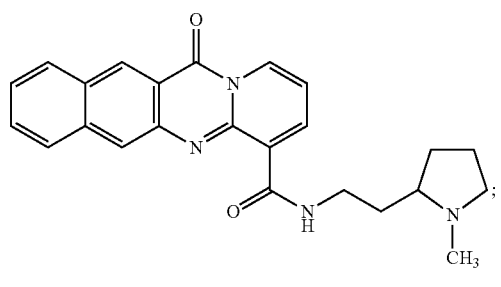
compound 12
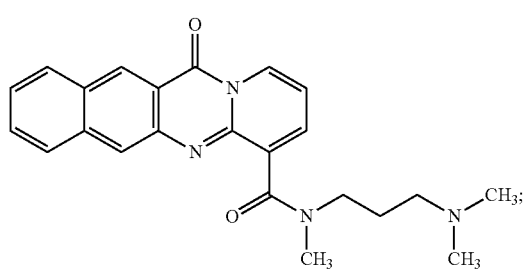
compound 13
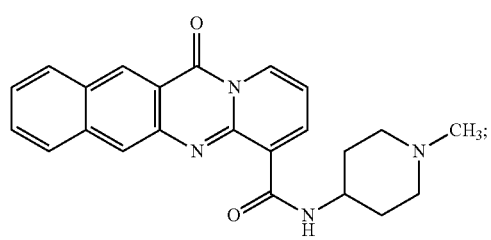
compound 14
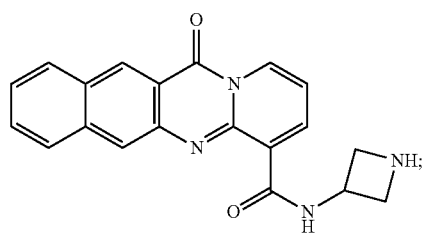
compound 17
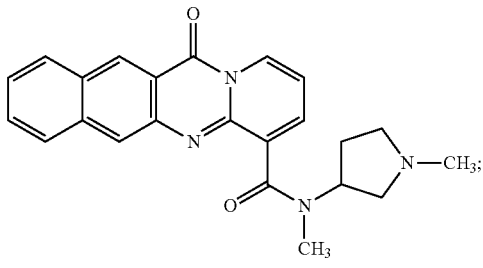
compound 19
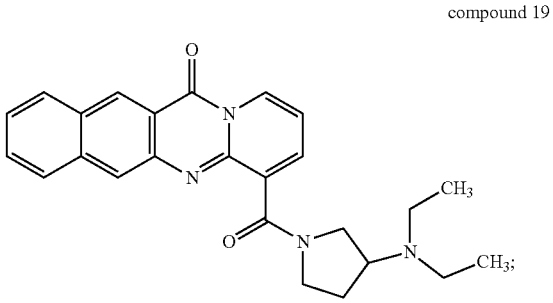
compound 22
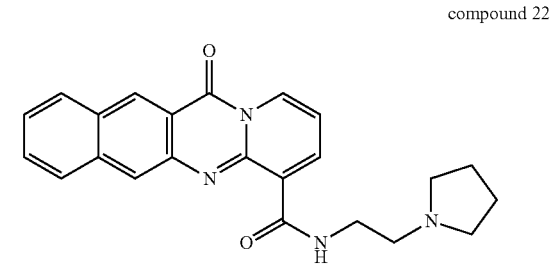
compound 23
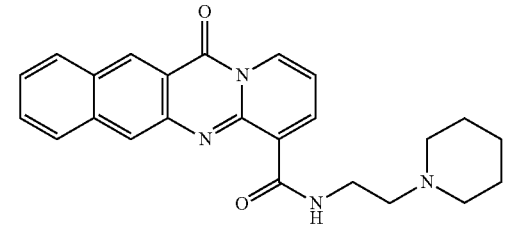
compound 24
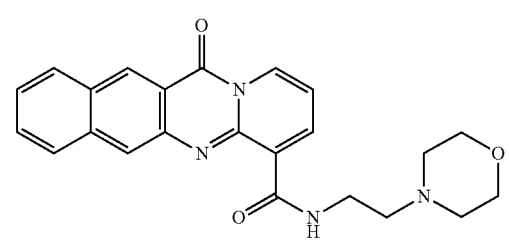
compound 25
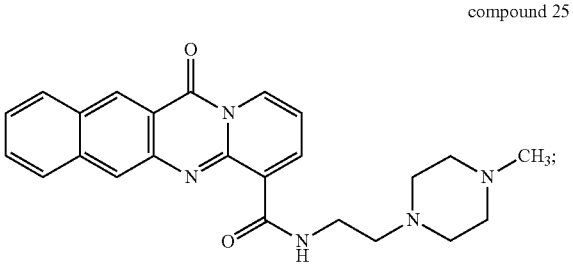

compound 27
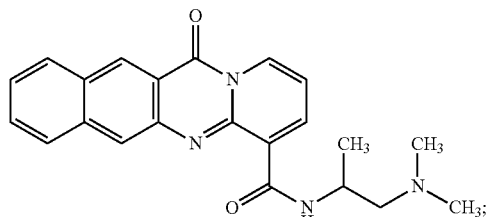
compound 28
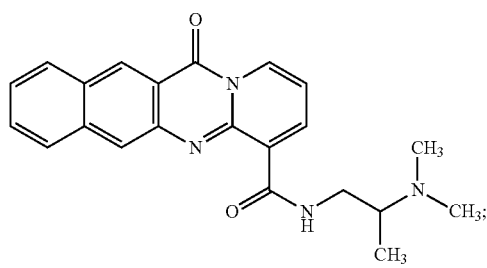
compound 29
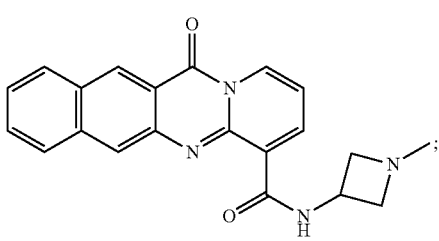
compound 30
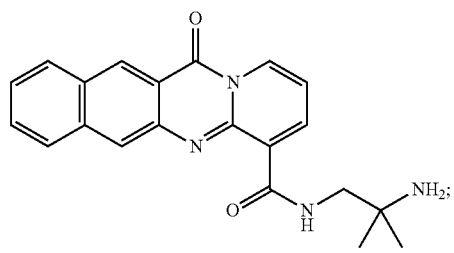
compound 31
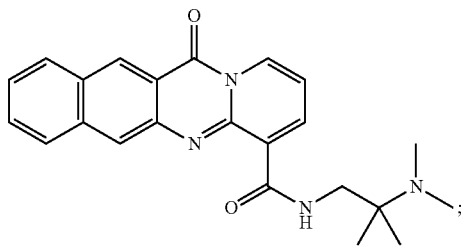
compound 32
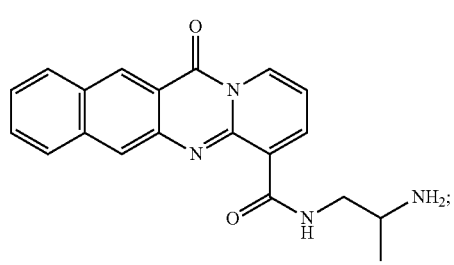
compound 33
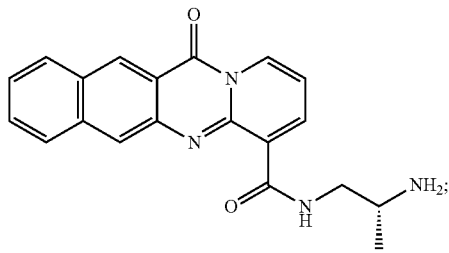
compound 34
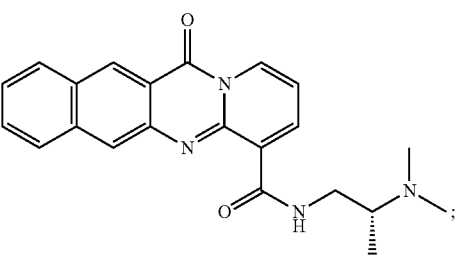
compound 35
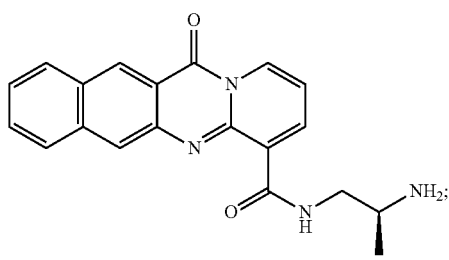
compound 36
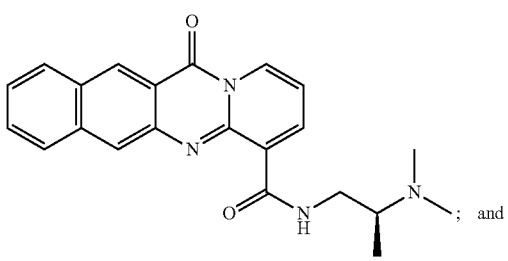
and
compound 37
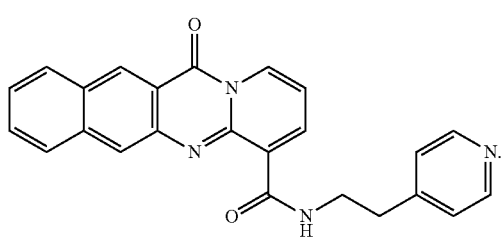
and a pharmaceutically acceptable carrier.

8. A compound selected from the group consisting of:

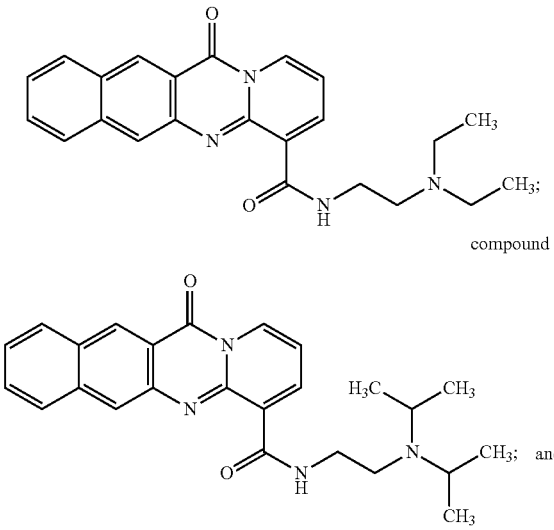

compound 20 compound 21 compound 26

9. A pharmaceutical composition comprising a compound of claim 8, and a pharmaceutically acceptable carrier.

10. The compound of claim 1, wherein $R_1$ is cyclopentyl or cyclohexyl.

11. The compound of claim 3, wherein $R_2$ is $C_1$-$C_6$ alkyl, which is substituted with one or more OH, $NH_2$, $NR_3R_4$, cyano, $SO_2R_3$, aryl, heteroaryl selected from the group consisting of imidazolyl, imidazolidinonyl, pyridyl, indolyl, oxazolyl, thiazolyl, and oxadiazolyl, cycloalkyl, or nitrogen-containing heterocycles; wherein $R_3$ and $R_4$, are independently selected from the group consisting of H, $C_1$-$C_6$ alkyl, and $C_1$-$C_4$ alkoxy alkyl.

* * * * *

UNITED STATES PATENT AND TRADEMARK OFFICE
CERTIFICATE OF CORRECTION

PATENT NO. : 11,001,581 B2
APPLICATION NO. : 15/126588
DATED : May 11, 2021
INVENTOR(S) : Laiho et al.

Page 1 of 3

It is certified that error appears in the above-identified patent and that said Letters Patent is hereby corrected as shown below:

In the Specification

In Column 1, Line 11, delete "International Application" and insert -- International Application No. --, therefor.

In the Claims

Claim 1: In Column 43, Line 4, delete "phosphoryl, phosphoryl," and insert -- phosphoryl, phosphonyl, --, therefor.

Claim 1: In Column 43, Lines 8-9, delete "ureide," and insert -- ureido, --, therefor.

Claim 5: In Column 44, Lines 25-36, please delete compound 1

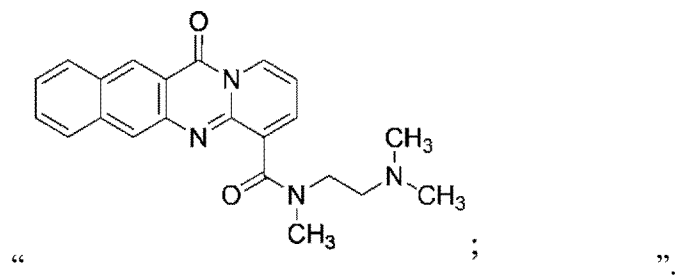

"                                  ;                    ".

Signed and Sealed this
Twenty-first Day of June, 2022

Katherine Kelly Vidal
*Director of the United States Patent and Trademark Office*

Claim 5: In Column 47, Lines 3-12, after " 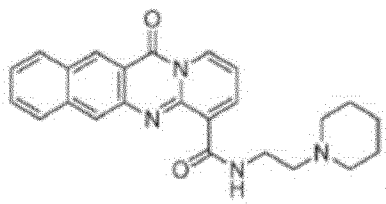 " insert -- ; --.
Claim 5: In Column 47, Lines 14-22, after " 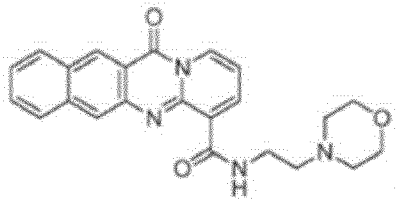 " insert -- ; --.
Claim 5: In Column 47, Lines 24-33, after " 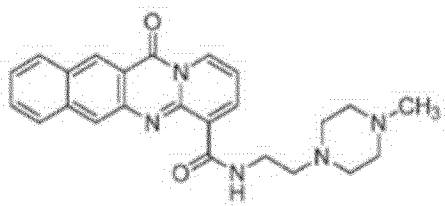 " insert -- ; --.
Claim 7: In Column 49, Line 40, delete "consisting of" and insert -- consisting of: --, therefor.
Claim 7: In Column 49, Lines 43-55, please delete
compound 1
" 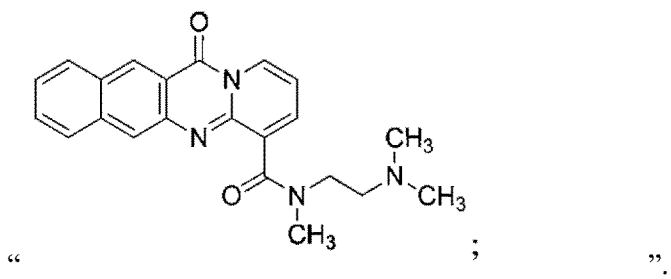 ; ".
Claim 7: In Column 52, Lines 27-35, after " 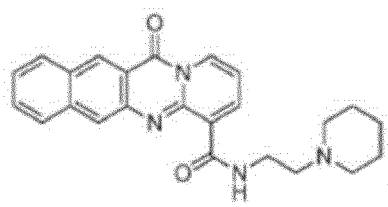 " insert -- ; --.

CERTIFICATE OF CORRECTION (continued)
U.S. Pat. No. 11,001,581 B2

Claim 7: In Column 52, Lines 38-46, after " 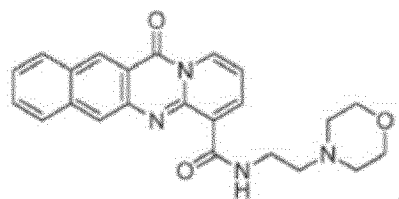 insert -- ; --.

Claim 7: In Column 52, Lines 48-56, after " 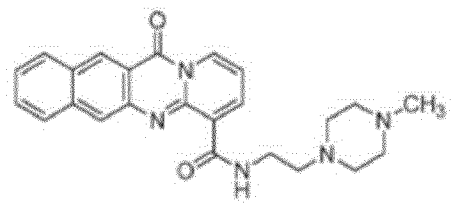 " insert -- ; --.

Claim 7: In Column 54, Lines 56-65, please delete " 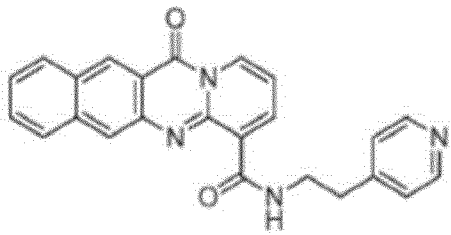 " and insert -- 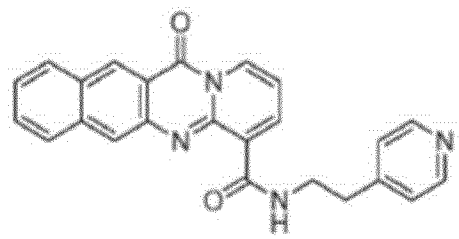 --, therefor.

Claim 11: In Column 56, Line 21, delete "imidazolidinoyl" and insert -- imidazolidinyl --, therefor.